(12) United States Patent
Hallinan et al.

(10) Patent No.: US 6,362,366 B1
(45) Date of Patent: *Mar. 26, 2002

(54) MANUFACTURING AND PROCESS CONTROL METHODS

(75) Inventors: Noel Hallinan; James A. Hinnenkamp, both of Cincinnati, OH (US)

(73) Assignee: Millennium Petrochemicals Inc, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/611,067

(22) Filed: Jul. 6, 2000

Related U.S. Application Data

(63) Continuation-in-part of application No. 09/216,330, filed on Dec. 18, 1998, now Pat. No. 6,103,934.

(51) Int. Cl.⁷ .......................... C07C 51/10; C07C 51/12
(52) U.S. Cl. ........................................ 562/517; 562/519
(58) Field of Search ................................ 562/517, 519, 562/520, 524

(56) References Cited

U.S. PATENT DOCUMENTS

| 4,000,170 A | 12/1976 | Forster et al. |
| 4,627,008 A | 12/1986 | Rosenthal |
| 5,121,337 A | 6/1992 | Brown |
| 5,317,379 A | 5/1994 | Ryan et al. |
| 5,468,961 A | 11/1995 | Gradon et al. |
| 5,596,992 A | 1/1997 | Haaland et al. |
| 5,604,132 A | 2/1997 | Capuano et al. |
| 5,691,701 A | 11/1997 | Wholstein et al. |
| 5,817,869 A | 10/1998 | Hinnenkamp et al. |
| 6,103,934 A1 * | 8/2001 | Hallinan et al. |

OTHER PUBLICATIONS

IR spectrum of methyl acetate from STN, 2001.*

* cited by examiner

*Primary Examiner*—Gary Geist
*Assistant Examiner*—Farhad Forohar
(74) *Attorney, Agent, or Firm*—Wood, Herron & Evans, LLP

(57) ABSTRACT

There is provided a process control method for the production of acetic acid by the catalyzed carbonylation of methanol and a process for the manufacture of acetic acid using the process control method. The process control method comprises measuring various reactor component concentrations, specifically the active catalyst species, methyl iodide, water and methyl acetate by means of an infrared analyzer, and adjusting in response thereto the concentrations of at least the catalyst species, methyl iodide and water to optimize the acetic acid reaction.

45 Claims, 27 Drawing Sheets

MANUFACTURING AND PROCESS CONTROL METHODS

CROSS-REFERENCE TO RELATED APPLICATION

This application is a continuation-in-part of U.S. patent application Ser. No. 09/216,330 filed Dec. 18, 1998 now U.S. Pat. No. 6,103,934 and entitled MANUFACTURING AND PROCESS CONTROL METHODS.

FIELD OF THE INVENTION

This invention relates to a method of improving process control in the manufacture of acetic acid, and a method of manufacturing acetic acid utilizing improved process control.

BACKGROUND OF THE INVENTION

In some chemical processes, it is necessary to monitor the progress of the chemical reaction and to adjust the supply of the reactants to ensure that the reaction proceeds as desired. The production of acetic acid, which is an important commercial commodity, is one such chemical process. One current method of manufacturing acetic acid, by carbonylation of methanol or its derivatives, such as methyl acetate or methyl iodide, involves a chemical reaction initiated by a Group 9 catalyst system, specifically as an iridium or rhodium coordination compound in the presence of an iodide and water. Carbonylation has become a preferred route to make acetic acid. Nevertheless, there are countervailing considerations which affect implementation of this process. First, the underlying reaction chemistry is intricate, involving a number of interrelated reactions, by-products and equilibria, all of which must be properly balanced, one against the other, to make the process practicable and maximize efficiency of raw material utilization. Also, the catalyst systems, such as coordination compounds of rhodium, iridium and the like, required for carbonylation are generally complex and expensive. Moreover, carbonylation catalyst systems are extraordinarily sensitive to changes in any number of reaction parameters which, in turn, adversely affect catalyst stability and activity.

It is known to manually sample the reactor effluent and perform a separate laboratory analysis of component concentrations using multiple instrumental and wet chemical methods. This procedure is labor intensive and time consuming, resulting in long time lapses between sampling and the characterization of the sample. This method of sample characterization realistically permits generation of a limited number of data points per day, typically about 3 to about 8. Also, because of the delay between sampling and generation of data, the sample characterization would provide an evaluation of a reactor system which may lag behind the actual status of the system by several hours.

Infrared analysis has been used for characterizing components of a chemical process stream. Infrared spectroscopy permits both qualitative and quantitative analyses. Sample analyses can be performed on both organic and inorganic species. Because nearly every molecule has an infrared spectrum, infrared spectroscopy is generally capable of characterizing every molecular component of a chemical process stream without destroying or otherwise modifying the components.

In monitoring the manufacture of acetic acid, the infrared energy absorption corresponding to the stretching frequencies of the hydroxyl and carbonyl groups of acetic acid generates broad absorption bands which tend to overlap, and therefore mask, the infrared bands indicating the presence of a rhodium or iridium catalyst.

In an effort to characterize, for example, rhodium in a rhodium-catalyzed carbonylation system, other methods of analysis have been employed, such as atomic absorption and inductively coupled plasma analysis. However, it is difficult to obtain rhodium concentration data of acceptable precision by either atomic absorption or inductively coupled plasma analysis. Both of these methods involve working up the sample to form a liquid matrix. The process of working up the sample also increases the risk of introducing air into the sample and thereby causing rhodium precipitation. Because of the unreliability of such analyses, the addition of rhodium to the reaction system has been based on an empirical relationship based on carbon dioxide production. However, this empirical relationship is subject to error when other operating conditions are changed, particularly at high operating rates.

It is highly desirable to be able to produce acetic acid under reduced water process conditions without sacrificing catalyst productivity and stability. Normally, the carbonylation process proceeds at a water level of about 11–14% by weight to maintain the catalyst in its active form. However, that quantity of water must later be separated from the acetic acid produced in the process, increasing processing time and cost. In U.S. Pat. No. 5,817,869 incorporated herein by reference in its entirety, the carbonylation system was modified to achieve low water carbonylation by adding a pentavalent Group 15, formerly Group VA, oxide. Group 15 includes the elements N, P, As, Sb and Bi. Although this new system successfully achieves high yields and reaction rates while stabilizing the active rhodium catalyst component, this modification to achieve low water processing increases the need for a reliable technique to determine the soluble rhodium content.

It is thus desirable to provide a reactant monitoring system that allows for more frequent monitoring of the chemical reaction in the production of acetic acid, particularly where low water processing techniques are utilized. In addition, because of the complexity of the catalyzed carbonylation reaction, monitoring of the catalyst concentration to the exclusion of other reactants is less likely to provide an accurate assessment of the status of the reaction system. It is thus also desirable to be able to monitor and adjust the concentration of up to all of the reactants of the system including the catalyst species based on direct analysis of the reactants. Further, it is desirable to utilize a reactant monitoring system to improve the efficiency of manufacturing acetic acid.

SUMMARY

The present invention is directed to a process for monitoring and controlling the concentration of reactor components in the production of acetic acid by the catalyzed carbonylation of methanol that measures the concentration values of at least the active catalyst species, methyl iodide, water and methyl acetate reaction components, with adjustment of at least methyl iodide, water and the active catalyst species to optimize the reaction. The invention is also directed to the process of manufacturing acetic acid based on the process control procedure described herein.

In a preferred embodiment of the present invention, acetic acid is produced by a low water carbonylation reaction incorporating a Group 15 oxide in the reaction solution, and the invention encompasses monitoring and adjusting the concentration of the Group 15 oxide. Preferably, monitoring is performed near in time to removal of sample from the reactor, and most preferably is conducted on-line. As described herein, on-line measurement refers to the analysis of a process solution in real time or substantially real time either by direct insertion of a probe into the process vessel of interest or by rapidly circulating process solution through an analyzer and subsequently returning this solution to the process. Off-line measurement refers to the irreversible removal of a sample from a process and subsequent analysis being performed on laboratory instrumentation. Further, it is preferred that adjustment of component concentrations and reaction parameters as required be performed substantially immediately following characterization of the sample. Preferably, this adjustment is performed automatically in response to the sample characterization. Finally, it is preferred that the sampling be performed often to minimize undesirable drift from optimum reaction efficiency.

These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

The method in its broader aspects is practiced by collecting a sample of an acetic acid reaction mixture containing at least methyl iodide, water, methyl acetate and an active catalyst species of a catalyst selected from the group consisting of rhodium and iridium; measuring the concentration of methyl iodide, water, methyl acetate and the active catalyst species in an infrared analyzer; and adjusting the concentration of at least methyl iodide, water, and the active catalyst species in the acetic acid reaction mixture in response to the measured concentrations of methyl iodide, water, methyl acetate and active catalyst species. The process of manufacturing acetic acid based on improved process control of at least these reaction components is also described.

Preferably the infrared analyzer is a Fourier Transform infrared spectrometer. Analysis of reaction components is conducted in the infrared cells which operate in one or more of the mid-infrared regions and the extended mid-infrared region. Preferably, the adjustment of concentrations of at least methyl iodide, water and the active catalyst species in the acetic acid reaction mixture produces a substantially constant concentration for each of the methyl iodide, water, methyl acetate and active catalyst species during the manufacture of acetic acid.

The process control is facilitated by frequent measurement of the reactant components in the acetic acid reactor. The frequency of measurement should be effective to maintain a substantially constant concentration of at least methyl iodide, water, methyl acetate and active catalyst species during the manufacture of acetic acid. It has been found that a measurement frequency of approximately thirty times per hour produces good results.

The active catalyst species may be the active species of either an iridium or rhodium catalyst. In the examples provided herein, the active species utilized was of a rhodium catalyst.

Figure 1:
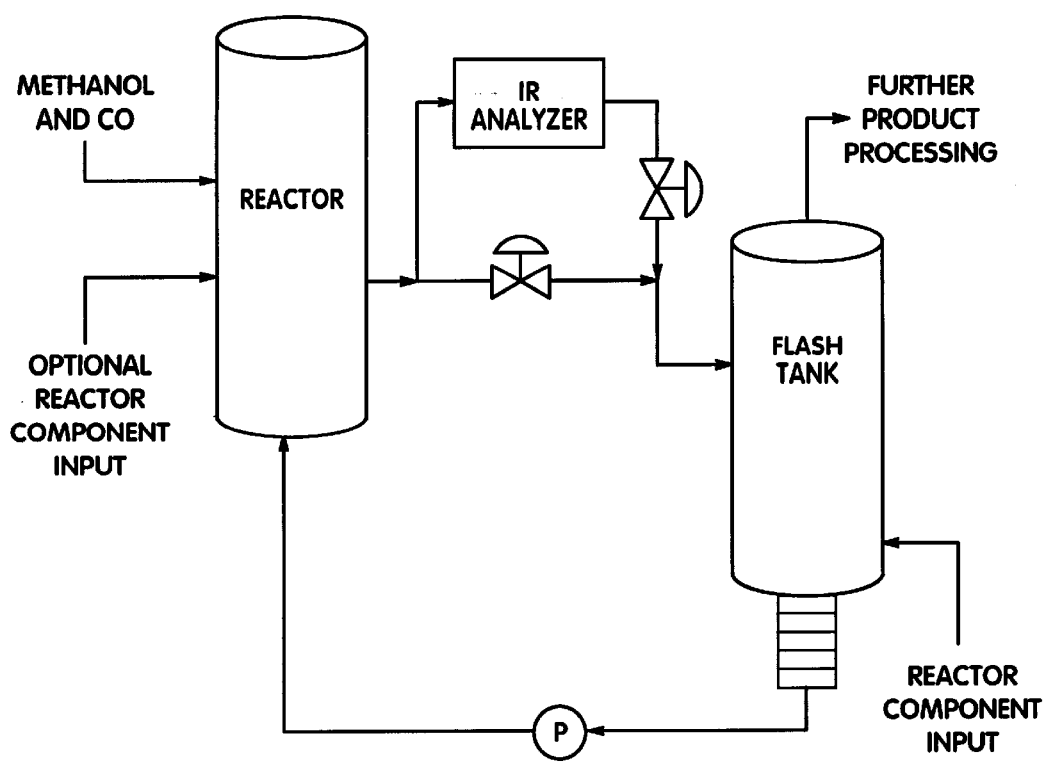
FIG. 1 is a schematic representation of one mode of the on-line analysis of the present invention.

FIG. 1 is a schematic representation of one mode of the present invention for monitoring on-line the carbonylation of methanol to acetic acid, and adjusting reactor components as necessary. To monitor the components of the reaction system for the production of acetic acid, a sample or slipstream is collected from the reactor effluent and transferred through an infrared analyzer to a low pressure flash tank. Alternatively, the sample may be collected in situ by insertion of a probe into the reactor or reactor slipstream. The sample is then analyzed, as will be discussed in detail hereafter, and the results fed to a display or control unit. The concentrations of one or more reactor components are adjusted in response thereto so as to optimize reaction efficiency. These reactor components mainly include water, methyl iodide (MeI), and rhodium catalyst (Rh(CO)$_2$I$_2^-$). Addition of one or more reactor components to the reactor is typically effected through the flash tank, though direct injection into the reactor is an option. Acetic acid produced in the reactor is withdrawn for purification or other processing through the flash tank. The pure acetic acid product is removed from the system, and most of the remaining components are recycled to the reactor. A small amount of byproducts are removed from the system and disposed of. Methyl acetate (MeOAc) levels in the system are generally adjusted indirectly by adjusting one or more of methyl iodide, active rhodium species or water concentration, and the reaction temperature. Alternatively, methyl acetate can be added directly to the reaction system.

The reaction system may optionally contain a pentavalent Group 15 oxide of the formula R$_3$M=O to generate acetic acid via a low water process, as disclosed in U.S. Pat. No. 5,817,869 entitled "Use of Pentavalent Group VA Oxides in Acetic Acid Processing", incorporated herein by reference in its entirety. In the formula R$_3$M=O, M is an element from Group 15 of the periodic table and each R is independently a substituted or unsubstituted alkyl, aryl, aralkyl or alkaryl group. Because the Group 15 element (formerly Group VA) is preferably phosphorus, as disclosed in that application, the pentavalent Group 15 oxide will hereafter be referred to as phosphine oxide or triphenyl phosphine oxide, though other oxides disclosed in U.S. Pat. No. 5,817,869 may be used. Phosphine oxide concentration may be analyzed and adjusted according to the principles of the present invention.

In the manufacture of acetic acid by carbonylation of methanol, the use of a transition metal catalyst, such as rhodium or iridium, will allow the reaction to proceed at greatly reduced pressures and temperatures compared to the uncatalyzed reaction. For ease of the discussion herein, a rhodium-catalyzed carbonylation system will be described. It is to be understood, however, that iridium-catalyzed systems are contemplated to be within the scope of the present invention. In the rhodium-catalyzed carbonylation system, methanol and carbon monoxide are brought into contact in a reactor in the presence of water, methyl iodide, acetic acid and a homogeneous rhodium catalyst. Rapid esterification of methanol with acetic acid leads to formation of methyl acetate and water and thus only trace amounts of methanol are detected in the reactor solution. The equilibrium reaction between hydrogen iodide and methyl acetate allows a steady state concentration of methyl iodide to be maintained in order to promote the reaction.

The homogeneous rhodium catalyst may be added to the system by means of a number of rhodium-containing components, which include, without limitation: RhCl$_3$; RhBr$_3$; RhI$_3$; RhCl$_3$.3H$_2$O; RhBr$_3$.3H$_2$O; RhI$_3$.3H$_2$O; Rh$_2$(CO)$_4$Cl$_2$; Rh$_2$(CO)$_4$Br$_2$; Rh$_2$(CO)$_4$I$_2$; Rh$_2$(CO)$_8$; Rh(CH$_3$CO$_2$)$_2$; Rh(CH$_3$CO$_2$)$_3$; Rh[(C$_6$H$_5$)$_3$P]$_2$(CO)I;

$Rh[(C_6H_5)P)]_2(CO)Cl$; Rh metal; $Rh(NO_3)_3$; $Rh(SnCl_3)$ $[(C_6H_5)_3P]_2$; $RhCl(CO)[(C_6H_5)_3As]_2$; $RhI(CO)[(C_6H_5)_3Sb]_2$; $[Y][Rh(CO)_2X_2]$, wherein X is $Cl^-$, $Br^-$ or $I^-$; and Y is a cation selected from the group consisting of positive ions from Group 1 of the Periodic Table of Elements, such as H, Li, Na and K, or Y is a quaternary ion of N, As or P; $Rh[(C_6H_5)_3P]_2(CO)Br$; $Rh[n-C_4H_9)_3P]_2(CO)Br$; $Rh[(n-C_4H_9)_3P]_2(CO)I$; $RhBr[(C_6H_5)_3P]_3$; $RhI[(C_6H_5)_3P]_3$; $RhCl[(C_6H_5)_3P]_3$; $RhCl[(C_6H_5)_3P]_3H_2$; $[(C_6H_5)_3P]_3Rh(CO)H$; $Rh_2O_3$; $[Rh(C_3H_4)_2Cl]_2$; $K_4Rh_2Cl_2(SnCl_2)_4$; $K_4Rh_2Br_2(SnBr_3)_4$; $[H][Rh(CO)_2I_2]$; $K_4Rh_2I_2(SnI_2)_4$ and the like. Preferably the rhodium species used herein is water or acetic acid soluble. Preferred compounds are $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, or $[H][Rh(CO)_2I_2])$ with $[H][Rh(CO)_2I_2]$, $Rh(CH_3CO_2)_2$ and $Rh(CH_3CO_2)_3$ being most preferred.

Under typical reactor conditions of temperature and pressure, the reaction chemistry is quite complex and several dependent chemical equilibria contribute to reaction rate, catalyst stability and reaction selectivity. The rhodium catalyst is preferentially present as the following coordination compound, $Rh(CO)_2I_2^-$, or $Rh^I$ as used herein. Oxidative addition of methyl iodide to $Rh^I$ leads to formation of transient acetyl iodide, $CH_3COI$, which is rapidly hydrolyzed by water to form acetic acid and hydrogen iodide.

Though acetic acid will be formed via this reaction, the rate of acid formation is diminished by the presence of several competing side reactions which remove key reactants from the reaction cycle. The most prominent of these side reactions is the water gas shift reaction in which rhodium catalyzes the formation of carbon dioxide and hydrogen from carbon monoxide and water. The consequences of this side reaction include increased carbon monoxide usage and the necessity for an increased reactor purge rate in order to remove excess carbon dioxide and to maintain a set partial pressure of carbon monoxide.

Under reaction conditions, rhodium will be present as a mixture of the active form $Rh^I$ and the inactive form, $Rh(CO)_2I_4^-$, or $Rh^{III}$ as used herein. The latter species is an intermediate in the water gas shift cycle. The presence of a steady state concentration of this $Rh^{III}$ species not only adversely affects the rate of acetic formation, but also leads to decreased catalyst stability as $Rh^{III}$ species are more prone to precipitation than $Rh^I$ species. Thus, maximizing rhodium as $Rh^I$ is a key step in improving methanol carbonylation technology.

Reactor conditions for the present invention encompass temperatures of about 170° C. to about 200° C. and a pressure of about 350 psig to about 450 psig. At higher temperatures, the reactor equipment components typically made from Hastelloy™ B2 are subject to unacceptable corrosion risk. At lower temperatures, the reaction rate is unacceptably slow.

In one embodiment, the temperature of the collected sample is controlled within a range so as to optimally both quench the reaction in the sample and prevent precipitation of any solids. If the temperature is too high, the carbon monoxide content becomes depleted through continued reaction in the sample. If the temperature is too low, one or more of $Rh^{III}$ and the optional phosphine oxide promoter could precipitate out. This precipitation will not only alter the measured concentration, but will also tend to cause blockages in the transfer lines.

One method of monitoring the reactor solution in situ is achieving sample collection by using an attenuated total reflectance (ATR) probe with a suitable crystal material. Transfer of light signal to the detector can be achieved by light pipe, chalcogenide fiber or other methods known to those skilled in the art of infrared spectroscopy. Using a similar analysis technique, this probe could optionally be inserted into the reactor or a reactor slipstream to provide on-line analysis capability. Alternately, a reactor slipstream is passed through an infrared analyzer equipped with either a flow through ATR cell or flow through transmission cell. Preferably, continuous flow is employed and reactor solution is subsequently returned to the reaction system via the (low pressure) flash tank. By using a back pressure regulator or similar device located after solution has passed through the cells, essentially no pressure drop occurs across the cells. This ensures that analysis is performed with minimal change from the reactor pressure thereby resulting in no degassing or bubble formation in the cells. These latter effects, if present, would severely impact solution component quantitation. The temperature of the slipstream can be maintained anywhere between ambient and process temperature. Thus, a temperature range of 20° C.–200° C. is contemplated. Optimal temperature is governed by several parameters, such as precipitation of solids, compatibility of cell window or crystal materials with process conditions, and controlling process reaction in the slipstream. The most preferred temperature range of the slipstream is 30° C.–120° C. It is generally undesirable to operate at or below 30° C. as select reactor components show increasing propensity to precipitate as temperature is lowered. It is also preferred to operate at or below 120° C. in order that reaction substantially quenches in the transfer lines, thus ensuring that the measured analyte concentrations are representative of the concentrations in the reactor immediately prior to sampling. Finally, optimal operating temperature is a function of the particular cell window material used.

Another alternative process control technique is laboratory off-line analysis of a reactor sample by FTIR. While not as desirable as the most preferred embodiment of real time measurement as provided by on-line analysis, laboratory FTIR does provide significant advantages over conventional off-line methods of analysis. In particular, all components can be measured simultaneously by one mid-infrared measurement. The conventional alternative analysis involves using gas chromatography, Karl Fischer, hygrometer, titrimetric methods and ICP or AA. In addition, ICP/AA requires extensive sample pretreatment prior to analysis. Thus, in terms of feedback for process control, reactor component concentrations as determined by FTIR can be available in as little as 7 minutes after sample receipt in the lab, compared to a minimum of 1 hour in the case of the non-FTIR methods. The sample can be analyzed at ambient pressure and temperature using either the probe or transmission cell technology described above.

Depending on the temperature employed, the cell window or crystal material can be selected from the group of materials including $CaF_2$, ZnS, sapphire, AMTIR (Se—Ge—As composite), Ge, ZnSe, Si, diamond, KRS-5 (thallium bromoiodide), or cubic zirconia. The nature of these materials in terms of composition, transmission ranges, and the like are well known to those skilled in the art of spectroscopy and are readily available in spectroscopic and vendor literature. In a preferred embodiment of this invention, involving transmission cell analysis of a slipstream, sapphire windows are used. Sapphire has the appropriate transmission range to allow the analysis to be performed. It also displays good mechanical strength, chemical resistance and resistance to etching in the process described hereinabove.

In the process of monitoring the status of the reaction, the sample to be analyzed is transferred from the reactor to the analyzer and ultimately to a flash tank, with the pressure decreasing from approximately 400 psig to about 20–30 psig in the flash tank. As described hereinabove, the bulk of the pressure drop occurs only after the reactor solution has passed through the cells. Generally, the differential pressure controls the movement of reactor solution from the reactor to the infrared analyzer and the flash tank. A differential of only about 10–15 psig is sufficient to transfer the sample from the reactor. A circulation pump may also be utilized to move the fluid through the transfer line, thus eliminating the need to decrease the pressure of the system. Alternatively, the sample material may be analyzed as a side stream from the reactor unit. This sample would be analyzed under the same conditions of temperature and pressure as the reactant material, and therefore, would not be susceptible to precipitation. However, the temperature would result in continued reaction, requiring that sample analysis be conducted promptly. All tubing, valving and the like contacting the reaction solution must be chemically inert to the reaction components and be capable of withstanding corrosive attack under reaction conditions. A representative manufacturing material is Hastelloy™ B2, a Ni—Mo—Fe alloy. Other suitable materials include Hastelloy™ B3 (also a Ni—Mo—Fe alloy) and zirconium.

A number of options are available as to how the monitoring of the acetic acid reaction components may be performed.

Monitoring can be carried out by analyzing in a combination of select spectral ranges of traditional mid (400–4000 $cm^{-1}$) and extended mid- (4000–7000 $cm^{-1}$) infrared regions. One option involves a dual transmission cell, dual detector setup in which reactor solution sequentially flows through both cells. These cells differ only in pathlength. One cell has a pathlength of 0.05–0.15 mm which allows for analysis in the spectral region between 1800–5600 $cm^{-1}$ and thereby encompasses portions of traditional mid- and extended mid-infrared regions. The second cell has a pathlength of 0.2–3.0 mm which allows for analysis only in the extended mid-infrared region. The different cell pathlengths are utilized to both counteract the highly absorbing nature of acetic acid and take advantage of the two different spectroscopic regions for reactant component characterization.

Optionally, monitoring of the reaction components can be carried out using a single transmission cell, single detector setup. Depending on the cell pathlength chosen, different spectral regions can be used. A cell of pathlength 0.05–0.15 mm as described above allows quantitation of all components absorbing in the spectral region between 1800–5600 $cm^{-1}$. This region is commonly referred to as the non fingerprint region and encompasses portion of both the traditional mid-infrared region and extended mid-infrared region as noted above. Alternately, a cell of much shorter pathlength, 0.005–0.015 mm allows access to both the non fingerprint region (1800–5600 $cm^{-1}$) and the fingerprint region, which is 1800–400 $cm^{-1}$. This shorter pathlength can also be effectively achieved by using an attenuated total reflectance (ATR) crystal rather than a transmission cell. As is known to those skilled in the art, utilization of a single cell or ATR crystal in analysis of the acetic acid reaction mixture involves accepting a compromise between the extent of the range of infrared spectrum analyzed and the quantitative accuracies of concentration of certain components in the mixture. Measurement accuracies and precisions differ for different reaction components in different spectral regions using different cell pathlengths. Thus, the accuracy and precision required for a particular analysis dictates the choice of type of cell or cells, pathlength and transmission range.

The following table, Table 1, shows the spectral regions where the nine solution chemical compounds described herein and constituting the primary components of the rhodium-catalyzed acetic acid reaction can be quantified.

TABLE 1

| Component | Extended Mid (4000–7000 $cm^{-1}$) | Non Finger-Print Mid (1800–4000 $cm^{-1}$) | Fingerprint Mid (400–1800 $cm^{-1}$) |
| --- | --- | --- | --- |
| $Rh^I$ | No | Yes | No |
| $Rh^{III}$ | No | Yes | No |
| $CO_2$ (Soln.) | No | Yes | No |
| Methyl Acetate | Yes | Yes | Yes |
| Methyl Iodide | Yes | Yes | Yes |
| RI, where R = H, Group 1, 6, 7, 9, 11, 12 Metals and I = iodide | Yes | Yes | Yes |
| Triphenyl Phosphine Oxide | Yes | Yes | Yes |
| $H_2O$ | Yes | Yes | Yes |
| Acetic Acid | No | No | Yes |

The flow rate to the analyzer is adjusted to optimize precision and accuracy of measurement and typically is about 10 to about 100 sccm.

Process control of the reaction for manufacturing acetic acid based on the information obtained in the analysis can be either manual or automatic. Preferably, the data obtained from the infrared analyzer is fed to a computerized control unit, which automatically adjusts the reactor components, specifically, rhodium, water, methyl iodide and triphenyl phosphine oxide, to achieve steady values for certain components. Alternatively, the data is fed to a display unit and is interpreted by an operator who adjusts reactor component concentrations manually.

The direct analysis of this type of sample from the reactor traditionally has been complicated by the sample composition, which includes both gas and liquid components. Another obstacle in obtaining accurate measurements relates to the presence of acetic acid in the system. Broadness of absorption peaks are pathlength dependent. Acetic acid exhibits carbonyl absorption in the 1400–1800 $cm^{-1}$ range of the infrared spectrum. With broadening, this absorption range overlaps with the absorption range of rhodium, which is at 1900–2100 $cm^{-1}$. Traditionally, this overlap has prevented the accurate quantitative analysis of rhodium.

In the present invention, the analysis of rhodium concentration, specifically the active rhodium species $Rh(CO)_2I_2^-$, i.e. $Rh^I$, is carried out in the mid-infrared region, which is from 4000 $cm^{-1}$ to 400 $cm^{-1}$. In addition to measuring the active species of rhodium, the infrared analyzer may also measure the inactive rhodium species $Rh(CO)_2I_4^-$, i.e. $Rh^{III}$, and $Rh(CO)I_4^-$, i.e. $Rh^{III}$ mono as used herein, and a total rhodium concentration may be obtained from the sum of the active and inactive species. Similarly, the infrared analyzer may also measure the concentration of methyl iodide and of iodide ions($I^-$) in the reactor solution, and a total iodide concentration may be obtained from the sum of $I^-$ and methyl iodide. The analysis of methyl iodide and water takes place preferably in the extended mid-infrared region, although the analysis may also take place in the mid-infrared region.

Methyl acetate has a spectroscopic signature which is very similar to that of the bulk acetic acid solvent. While quantitation can be carried out in any of the extended mid, non fingerprint or fingerprint regions, excellent results can be achieved in the fingerprint region using an ATR cell or in the extended mid region using a transmission cell of pathlength 0.2–1.0 mm.

To facilitate analysis via infrared spectroscopy of the components in the reaction mixture, particularly where the infrared peaks for individual components tend to overlap or are not clearly defined, chemometric techniques can be utilized. Chemometrics is a branch of chemical analysis utilizing statistics wherein algorithmic relationships and mathematical logic are incorporated to obtain a calibration model involving multi-variate analysis. The term multivariate analysis refers to the relation of the concentration of a component in a solution to many infrared wavelengths or frequencies. Software products are commercially available which permit ready application of chemometric techniques. Representative products include PIROUETTE™, from Infometrix, Seattle, Wash. The general steps involved in developing chemometric calibration models are well known to those skilled in the art. Also, the American Society for Testing and Materials (ASTM) has published a document titled "Standard Practices for Infrared Multivariate Analyses (No. E1655-94)", incorporated herein by reference in its entirety, in which recommended guidelines are provided.

To obtain a good chemometric calibration model it is important to properly choose the calibration standards. A large number of calibration standards may need to be prepared and analyzed where there is a broad weak signal for the component of interest which is overlapped with signals from other components. The number can be in the range of 30 to 300. To create an accurate calibration model, a number of calibration standards are prepared, each containing all of the components normally present in the reactor solution. Some or all of these components are to be eventually analyzed by infrared spectroscopy. The components of individual standards are independently varied by concentration to randomize any bias or interferences that one component might have on another. The maximum and minimum concentration values expected in the reactor solution serve as the boundary limits for the individual component concentrations. After the standards are prepared they are sequentially injected into the infrared analyzer and a spectroscopic signal is collected. A previously collected spectrum of acetic acid is subtracted from the individual calibration solution spectra to remove as far as possible the signals attributed to acetic acid. Generally, the individual spectra for the calibration standards are first converted into digitized format and then set up in a spreadsheet with the corresponding concentrations of the component which is to be measured. Partial Least Squares (PLS) regression methods are then used to fit the data. Ultimately the accuracy of the calibration model is tested by comparing concentrations of the reaction components obtained from an on-line analyzer during an actual process run with the concentrations obtained by actually sampling the reactor and analyzing for component concentration using independent off-line analytical methods.

One advantage of the inventive process is the ability to rapidly determine the concentrations of rhodium, methyl iodide, water an methyl acetate to generate more reliable information on the status of the reaction and thereby avoid conditions of excessively high catalyst usage. The instant invention is capable of measuring component concentrations essentially in real time, and also allows for more frequent sampling. By providing information which allows manual or automatic adjustment of concentration and other process parameters, the inventive process can improve rhodium catalyst efficiency and utilization of the reactants thereby decreasing the cost of manufacturing acetic acid while maintaining product quality.

A corollary advantage of the process control method is the ability to confirm the information provided from the rhodium catalyst measurement by the concentration measurement of the other reactants. Monitoring the concentration of other reactants present in larger quantity in the reactor permits a cross-check of the reaction conditions and a more detailed understanding of the reaction status.

In practicing the invention, measurement of rhodium, methyl iodide, water, methyl acetate and other reactor components can be made as often as every one to two minutes, allowing the process control to very closely track the actual operating conditions within the reactor. This is a substantial improvement over the procedure of making the same measurements off-line.

In the low water carbonylation of methanol to acetic acid, the reactor effluent will also include a significant amount of phosphine oxide. The concentration of phosphine oxide is also capable of being measured and adjusted by the process control method of the present invention. The phosphine oxide promoter can be analyzed in the infrared ranges as specified in Table 1 above.

It is important that the monitoring process accurately reflect the composition of the reaction solution. Several examples of the testing of various chemometric calibration models developed on either laboratory or on-line infrared instrumentation are laid out below.

Figure 2A:
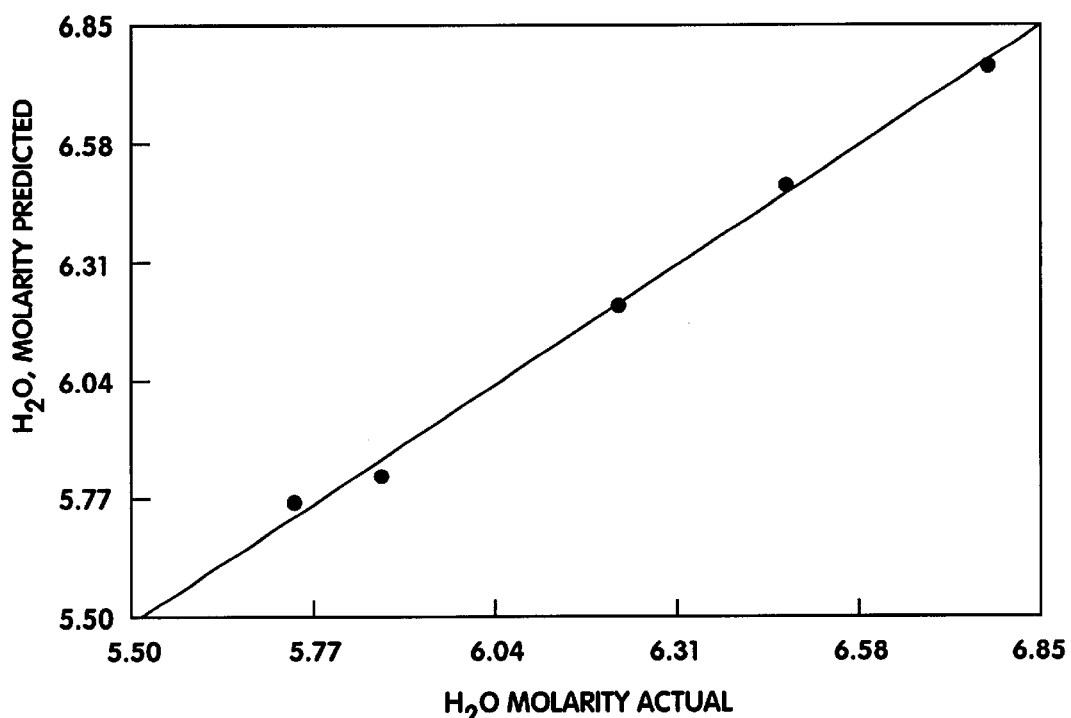
FIG. 2A is a correlation plot of actual vs. predicted concentration values showing the validation of the laboratory mid-infrared calibration model for water.
Figure 2B:
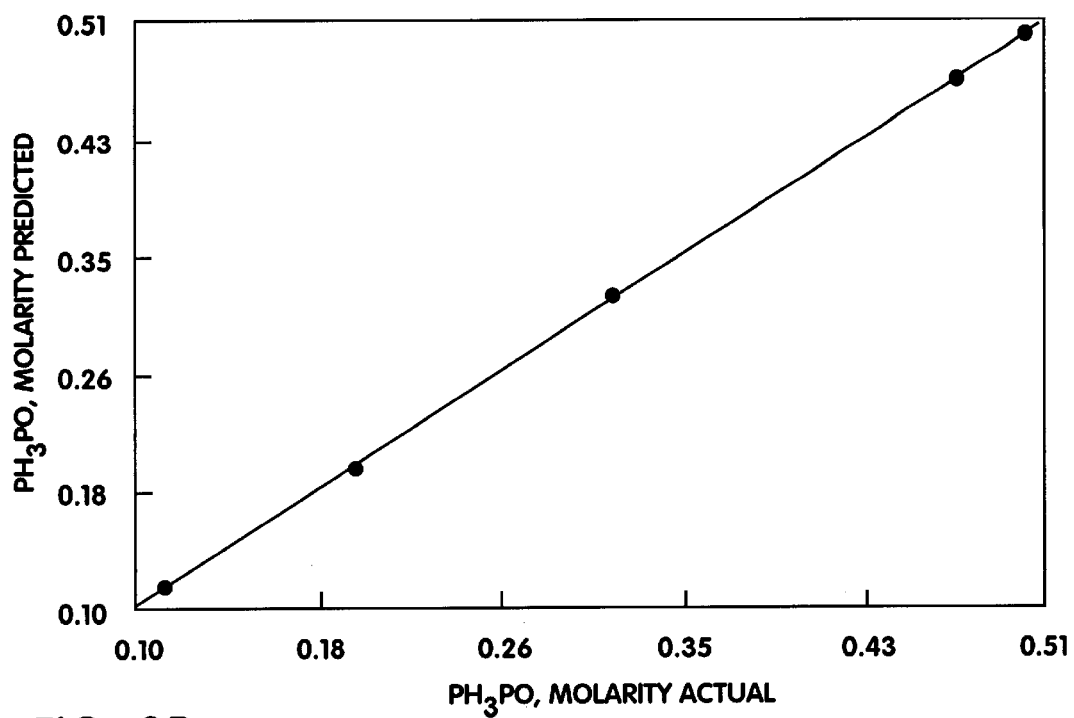
FIG. 2B is a correlation plot of actual vs. predicted concentration values showing the validation of the laboratory mid-infrared calibration model for triphenyl phosphine oxide ($Ph_3PO$)

To validate each of the chemometric calibration models developed on laboratory FTIR, five solutions were prepared, each containing known, differing amounts of phosphine oxide, water, methyl acetate, methyl iodide, hydrogen iodide and acetic acid, and each having a known measured density. These solutions were then analyzed quantitatively for molar concentration and density, with three measurements being recorded for each sample. The results tabulated below in Table 2 show close agreement between actual and predicted values for all components and also show good agreement between each of the three measurements performed for each component in each solution. For illustration purposes, this data is also represented in graphical format for water and triphenyl phosphine oxide in FIGS. 2A and 2B, respectively.

TABLE 2

Accuracy and Precision of Laboratory Mid-infrared Calibration Models Five Prepared Samples of Known Composition Were Used

| Sample # | $Ph_3PO$ (Molarity) | | $H_2O$ (Molarity) | | MeI (Molarity) | | $I^-$ (Molarity) | | MeOAc (Molarity) | | Density (g/ml) | |
| --- | --- | --- | --- | --- | --- | --- | --- | --- | --- | --- | --- | --- |
| | Actual | Predicted | Actual | Predicted | Actual | Predicted | Actual | Predicted | Actual | Predicted | Actual | Predicted |
| 1 | 0.47 | 0.468 | 6.47 | 6.49 | 0.61 | 0.64 | 0.029 | 0.043 | 0.101 | 0.092 | 1.104 | 1.104 |
| | | 0.466 | | 6.49 | | 0.637 | | 0.039 | | 0.095 | | 1.104 |
| | | 0.467 | | 6.48 | | 0.631 | | 0.042 | | 0.091 | | 1.102 |

TABLE 2-continued

Accuracy and Precision of Laboratory Mid-infrared Calibration Models Five Prepared Samples of Known Composition Were Used

| Sample # | $Ph_3PO$ (Molarity) Actual | Predicted | $H_2O$ (Molarity) Actual | Predicted | MeI (Molarity) Actual | Predicted | $I^-$ (Molarity) Actual | Predicted | MeOAc (Molarity) Actual | Predicted | Density (g/ml) Actual | Predicted |
|---|---|---|---|---|---|---|---|---|---|---|---|---|
| 2 | 0.112 | 0.118 | 6.77 | 6.73 | 0.677 | 0.68 | 0.322 | 0.34 | 0.251 | 0.24 | 1.127 | 1.125 |
|   |       | 0.117 |      | 6.79 |       | 0.689 |       | 0.32 |       | 0.246 |       | 1.123 |
|   |       | 0.116 |      | 6.78 |       | 0.67  |       | 0.31 |       | 0.243 |       | 1.122 |
| 3 | 0.315 | 0.316 | 5.74 | 5.75 | 0.771 | 0.761 | 0.205 | 0.224 | 0.403 | 0.399 | 1.13  | 1.128 |
|   |       | 0.315 |      | 5.75 |       | 0.764 |       | 0.216 |       | 0.41  |       | 1.129 |
|   |       | 0.32  |      | 5.8  |       | 0.751 |       | 0.183 |       | 0.407 |       | 1.127 |
| 4 | 0.198 | 0.198 | 6.22 | 6.21 | 0.846 | 0.841 | 0.418 | 0.428 | 0.606 | 0.616 | 1.153 | 1.151 |
|   |       | 0.196 |      | 6.17 |       | 0.847 |       | 0.397 |       | 0.598 |       | 1.149 |
|   |       | 0.197 |      | 6.25 |       | 0.835 |       | 0.441 |       | 0.599 |       | 1.15  |
| 5 | 0.502 | 0.499 | 5.87 | 5.93 | 0.844 | 0.821 | 0.15  | 0.146 | 0.899 | 0.921 | 1.135 | 1.135 |
|   |       | 0.498 |      | 5.82 |       | 0.823 |       | 0.153 |       | 0.91  |       | 1.134 |
|   |       | 0.497 |      | 5.82 |       | 0.832 |       | 0.132 |       | 0.916 |       | 1.134 |

Figure 3:
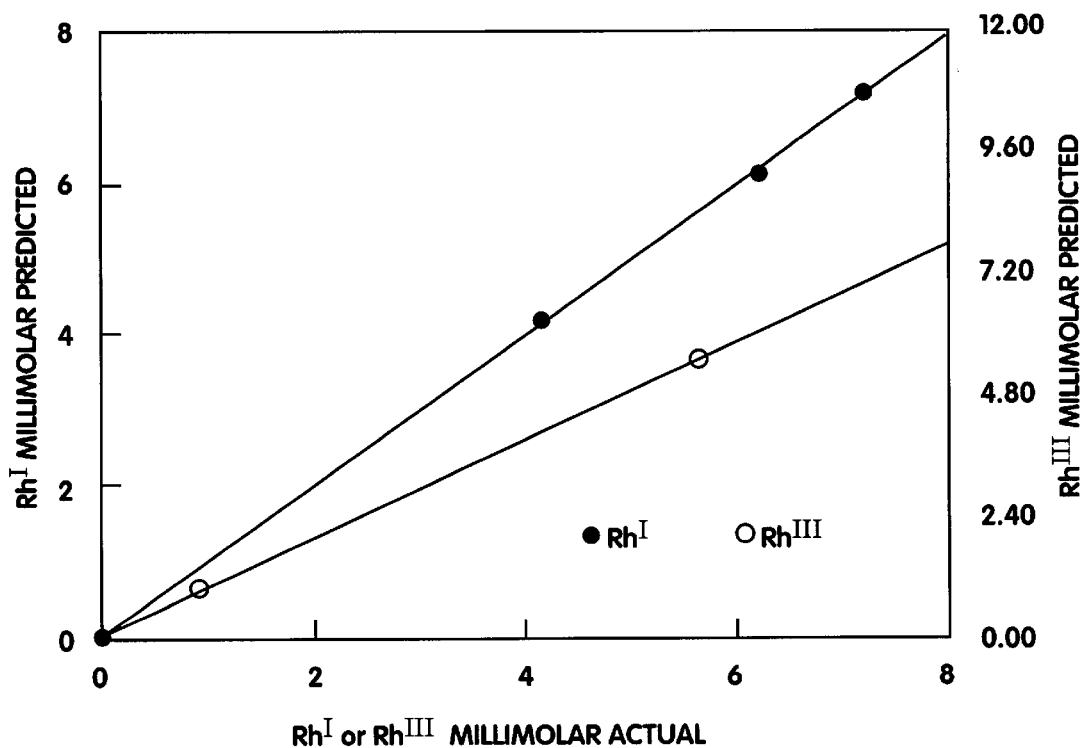
FIG. 3 is a correlation plot of actual vs. predicted values showing the validation of the on-line mid-infrared calibration model for active rhodium species ($Rh^I$) and inactive rhodium species ($Rh^{III}$)

To validate the chemometric calibration models developed for rhodium on the on-line analyzer, solutions of known $Rh^I$ or $Rh^{III}$ concentration were prepared in the laboratory and subsequently injected into an on-line analyzer and quantified. The on-line analyzer is described in more detail in Example 1. The actual vs. predicted values are tabulated below in Table 3 and represented graphically in FIG. 3. Again, excellent agreement was observed.

TABLE 3

| SAMPLE # | ACTUAL $Rh^I$ (mMolar) | PREDICT $Rh^I$ (mMolar) | ACTUAL $Rh^{III}$ (mMolar) | PREDICT $Rh^{III}$ (mMolar) |
|---|---|---|---|---|
| 6 | 0.00 | −0.06 | | |
| 7 | 4.14 | 4.18 | | |
| 8 | 6.19 | 6.15 | | |
| 9 | 7.17 | 7.22 | | |
| 10 | | | 0.89 | 0.92 |
| 11 | | | 5.64 | 5.53 |

Figure 4:
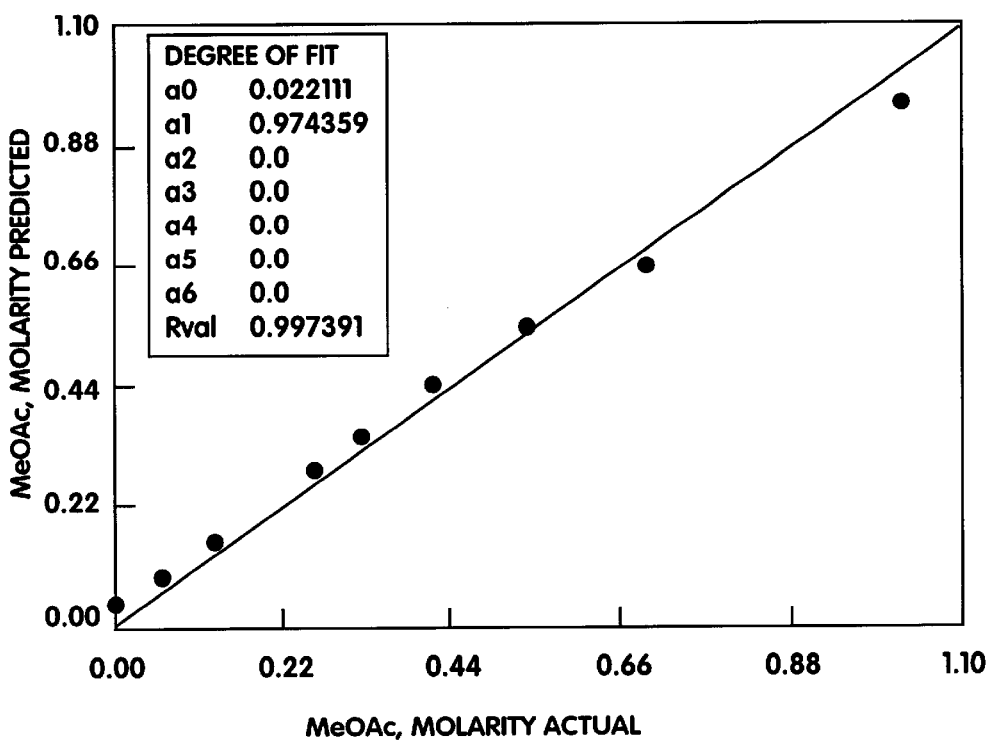
FIG. 4 is a correlation plot of actual versus predicted values showing the validation of the on-line extended mid-infrared calibration model for methyl acetate (MeOAc)

To validate the chemometric calibration model developed for methyl acetate on the on-line analyzer, multi-component solutions of known methyl acetate concentration were prepared in the laboratory and injected into the on-line analyzer and quantified. The actual versus predicted values are tabulated below in Table 4 and represented graphically in FIG. 4. Excellent agreement is observed.

TABLE 4

| Sample # | Actual MeOAc (Molar) | Predict MeOAc (Molar) |
|---|---|---|
| 12 | 0.00 | 0.032 |
| 13 | 0.064 | 0.087 |
| 14 | 0.133 | 0.150 |
| 15 | 0.264 | 0.284 |
| 16 | 0.326 | 0.350 |
| 17 | 0.415 | 0.450 |
| 18 | 0.541 | 0.550 |
| 19 | 0.690 | 0.662 |
| 20 | 1.020 | 0.967 |

Another approach to verification of calibration models is to compare the concentration values predicted by on-line models during an actual process run with the concentration values obtained by independent off-line methods of analysis. These data can be obtained by manually sampling the continuous bench scale reactor at random periods, analyzing these samples by conventional instrumental and wet chemical methods and comparing the predicted values with the values predicted on-line at the exact time of manual sampling. Thus, methyl iodide and methyl acetate concentrations determined by on-line infrared analysis were compared with off-line gas chromatography using a capillary gas chromatograph equipped with a flame ionization detector. Off-line water concentration was measured by the Karl Fischer technique. Off-line rhodium concentration was measured by the inductively coupled plasma (ICP) technique after work up of the reactor sample. Off-line phosphine oxide concentration was measured by $^{31}P$ NMR. Off-line $I^-$ was measured by an iodide selective electrode or by titration with silver nitrate.

FIG. 5 contains several plots (FIGS. 5A–5F) for this method of verification. As each of the independent off-line methods of analysis (iodide selective electrode, gas chromatography, $^{31}P$ NMR, inductively coupled plasma spectroscopy and Karl Fischer water determination) all have separate and different accuracy and precision limits, the most meaningful interpretation of the correlations is to look for any consistent bias of overprediction or underprediction for each component. If no such bias exists, and if the data can be linearly fitted, then the R factor or correlation coefficient is a valid indicator of the degree of fit between respective on-line and off-line analyses. The R factors annotated in the graphs in FIG. 5 are all>0.99, indicating that on-line analysis by FTIR is at least as good as off-line measurements by other analytical methods. The great advantage of the on-line method is that the sampling frequency is at least 100 times greater compared to off-line methods and data is obtained in real time in terms of process control.

The monitoring process of the instant invention is also capable of measuring carbon dioxide concentration as a dissolved gas in the acetic acid reaction solution. Carbon dioxide production is inversely related to the selectivity of the process of acetic acid formation as it is produced along with hydrogen in the competing and undesirable water gas shift (WGS) reaction. The more conventional method of measuring the extent of the WGS reaction is by analyzing the hydrogen content of the reactor vent gas stream by mass spectrometry. The ability to quantify the WGS reaction by the same technique as for other reactor solution components, i.e. on-line infrared, allows it to be easily tied in to any process control loop built around on-line infrared analysis. In order to verify that carbon dioxide solution concentration as determined by on-line infrared analysis correlates with vent gas hydrogen concentration as determined by mass spectrometry, continuous bench scale reactor data for both methods were compared over a period of 44 hours run time during which water concentration was varied from 5.5 molar to 3 molar leading to significant changes in the extent of WGS reaction. The reactor was run under the conditions set out below:

Temperature=185° C.

Pressure=400 psig

Methyl iodide concentration=0.75 Molar

Triphenyl phosphine oxide concentration=0.5 Molar

Rhodium concentration=5.5 Millimolar

Methanol feed rate=220 g/hr

Figure 6:
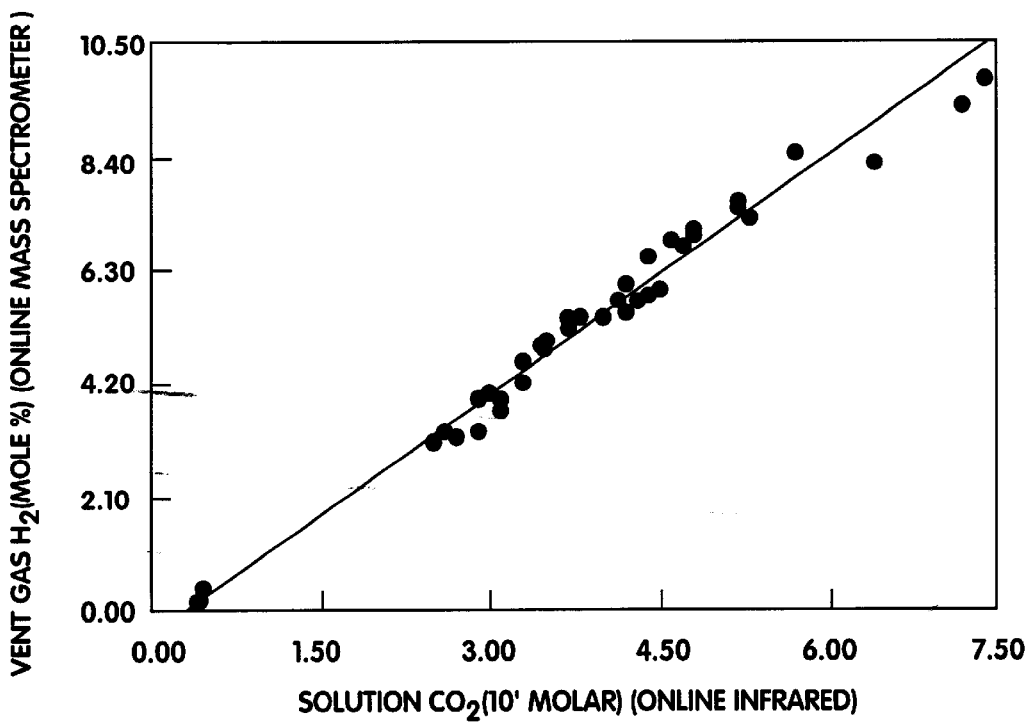
FIG. 6 is a correlation plot of bench scale reactor data for carbon dioxide solution concentration determined by on-line infrared vs. vent gas hydrogen concentration determined by mass spectrometry.
Figure 7:
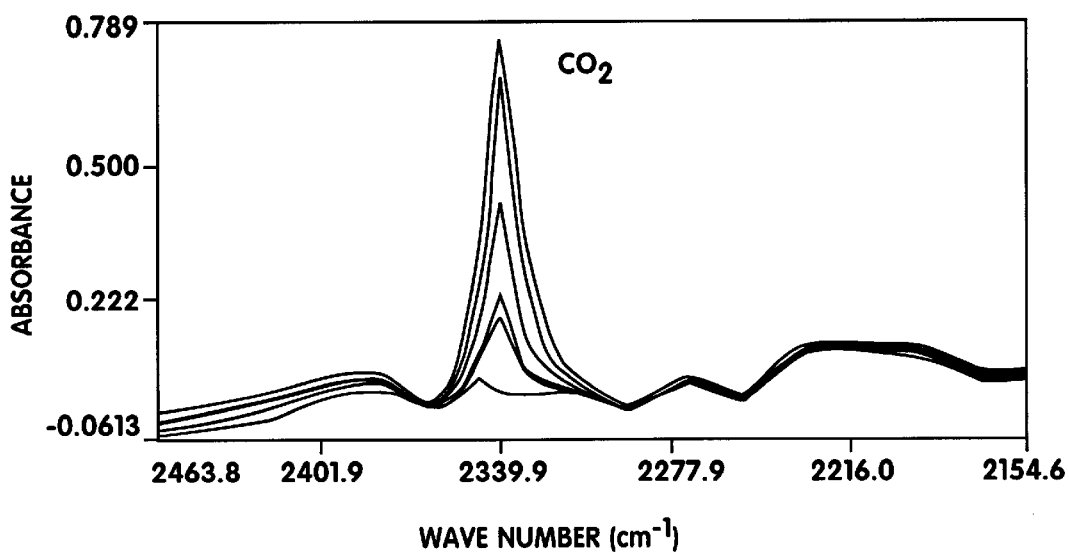
FIG. 7 is an overlay of on-line mid-infrared spectra showing the $CO_2$ peak intensity as it relates to reactor water concentration.

The correlation plot in FIG. 6 shows excellent agreement between the two techniques. FIG. 7 contains several overlaid mid-infrared spectra showing the changes in intensity of the $CO_2$ peak.

EXAMPLES

The following examples illustrate the step-by-step procedures employed in choice of calibration standards, data collection, correlation of spectral data with component concentration and development of calibration models. The examples show how these procedures are incorporated into the acetic acid manufacturing process for analysis of methyl acetate. Similar procedures were used in obtaining calibration models for other components.

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure

Example 1

Sixty calibration standards were prepared, each containing all of the components (other than rhodium and HI) normally present in a reactor solution. The concentrations of these components were independently varied to randomize any bias or interferences that one component might have on another. The concentration ranges shown below were chosen to reflect minimum and maximum values expected in actual process solution.

Acetic acid=10–12 molar

Water=2–7 molar

Methyl iodide=0.4–1.4 molar

Methyl acetate=0–1.0 molar

Triphenyl phosphine oxide=0–1.0 molar

These solutions were sequentially injected into an on-line FTIR analyzer. A detailed description of this analyzer is contained in Example 5. The solutions were maintained at 110° C. and 400 psi and were run through a 0.5 mm pathlength transmission cell equipped with 2 mm thick sapphire windows. The spectroscopic signal was collected by an indium arsenide (InAs) detector. An acetic acid reference spectrum was electronically subtracted from the calibration solution spectra to remove as far as possible all of the signals arising from acetic acid.

Figure 8:
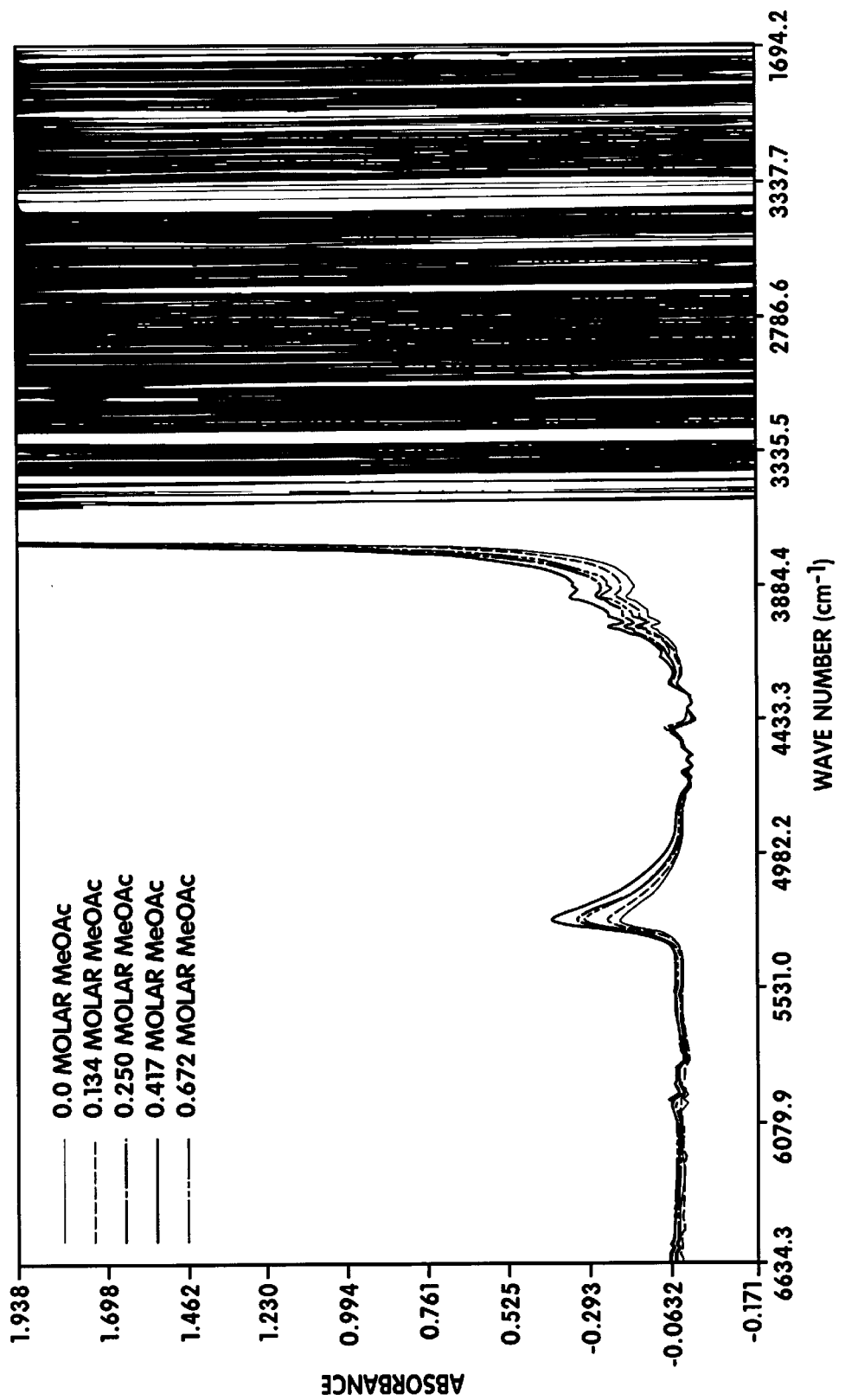
FIG. 8 is an overlay of on-line extended mid-infrared spectra of calibration solutions showing where totally absorbing regions occur.

Several overlaid spectra are shown in FIG. 8. These spectra represent different calibration solutions in which the methyl acetate concentration ranges from 0–0.67 molar. A number of features are evident. Even with acetic acid background subtraction, the region below 3800 $cm^{-1}$ is totally absorbing. This is partially due to the large acetic acid absorptions in this region at this pathlength but is also due to greatly reduced sensitivity of the InAs detector in this region. The region from about 3800 to 7000 $cm^{-1}$ (generally referred to as the extended mid-infrared region), is much cleaner.

Figure 9:
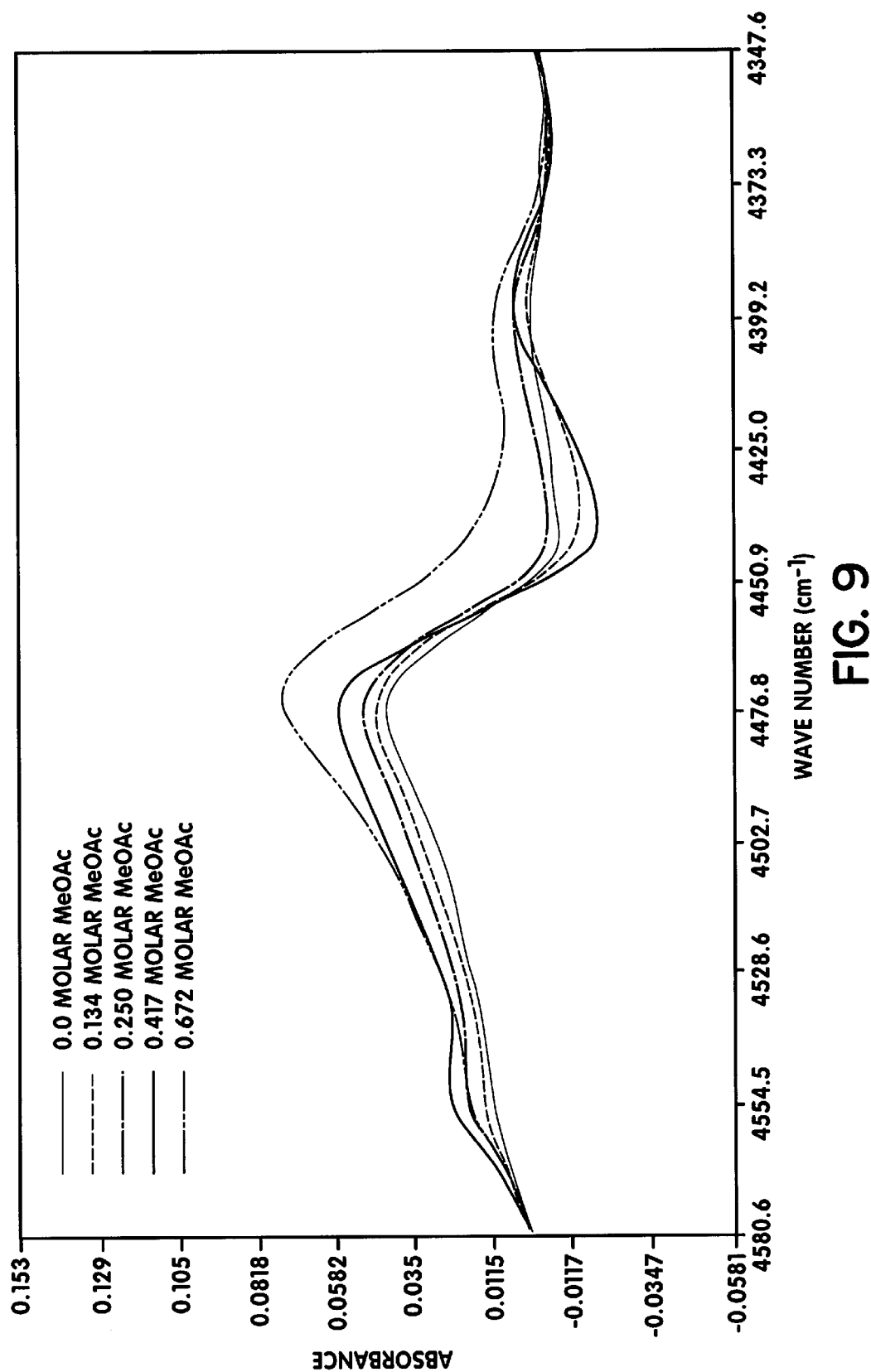
FIG. 9 is an expanded view of FIG. 8 showing a broad peak at 4480 $cm^{-1}$ associated with methyl acetate.

An expanded view of a small region of the spectra in FIG. 8 is shown in FIG. 9. In this Figure, the indicated broad peak at around 4480 $cm^{-1}$ is associated with methyl acetate. This band may result from stretching in the ($C—O—CH_3$) moiety of methyl acetate. It should also be noted that even for the spectrum with no methyl acetate, there is still an absorption band of considerable intensity at this point. This is more than likely due to residual acetic acid absorbances resulting from incomplete subtraction at this point. As this residual acetic acid absorbance will be different for all sixty solutions, the contribution it makes to the methyl acetate band will also be different.

A commercially available chemometric software package, PIROUETTE™, available from Infometrix was used for calibration model construction. The spectral files are first converted into digitized format and then set up in a spreadsheet with the corresponding methyl acetate concentrations. Partial Least Squares (PLS) regression methods are then used to fit the data. A complete explanation of the data manipulation including the mathematical background behind PLS regression is included in the software manual for PIROUETTE™.

Figure 10A:
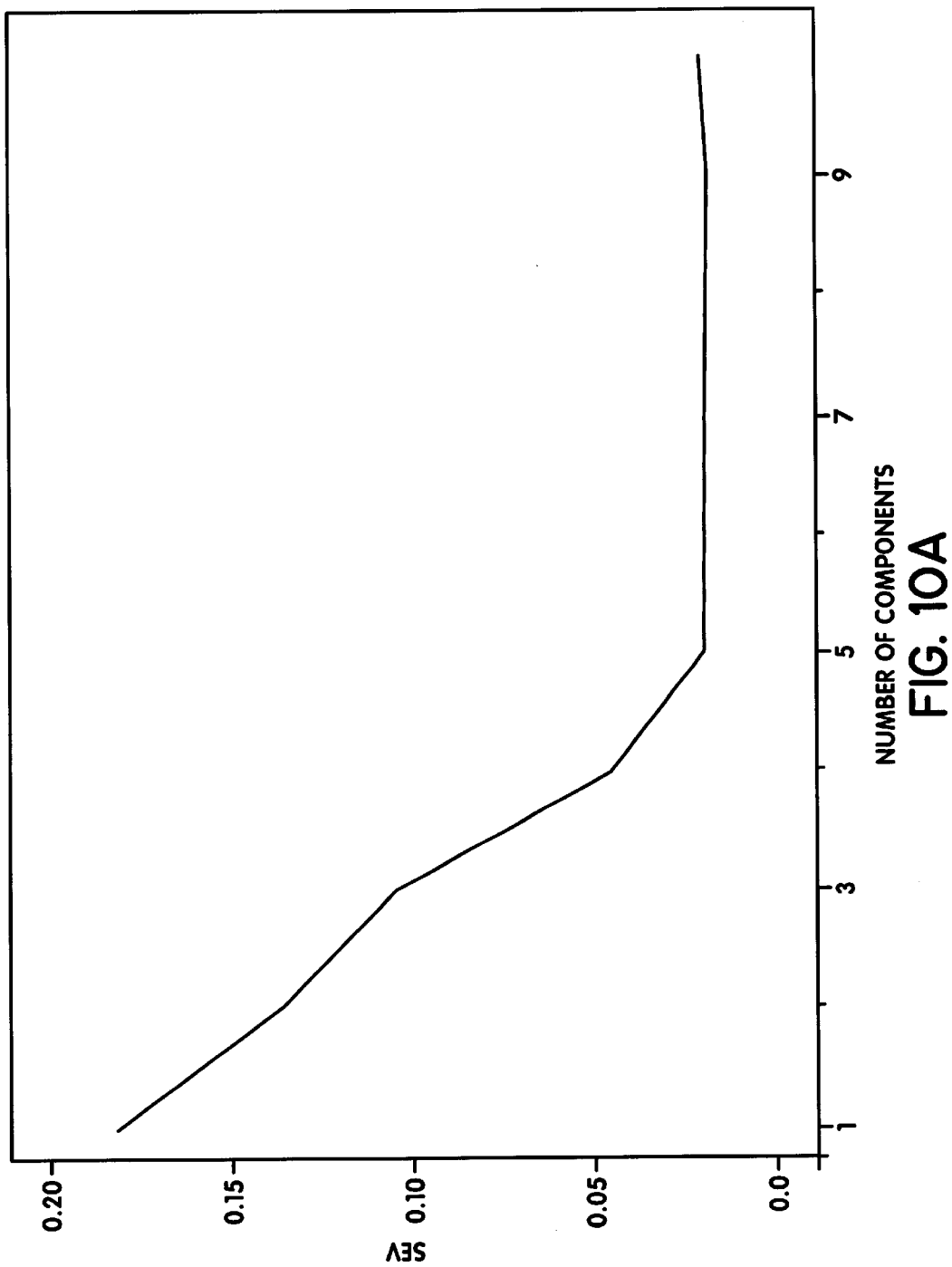
FIG. 10A is a cross validation plot generated by PIROUETTE™ for methyl acetate from the spectroscopic data obtained in FIG. 8.

The spectral region chosen for model construction was from 4600 to 4100 $cm^{-1}$. FIG. 10A illustrates the results of a cross-validation procedure automatically run by the software during the PLS regression. In cross-validation, one sample from the calibration set is temporarily left out and the remaining samples are used to create a model. From this model, a prediction is made of the methyl acetate concentration associated with the left-out sample, and the residual (difference between actual and predicted) recorded. Another sample is then excluded, a new model is made, and a new prediction and residual are generated. The procedure is repeated until every sample has been left out once. The resulting plot in FIG. 10A in which SEV refers to Standard Error of cross Variance, can then be used to determine the optimal number of factors to include in the model. The optimal number of factors will be associated with the minimum error in the SEV. This minimum error is then representative of the accuracy one might expect in analyzing a solution using this model. From FIG. 10A, an accuracy of about ±0.025 molar can be estimated.

Figure 5A:
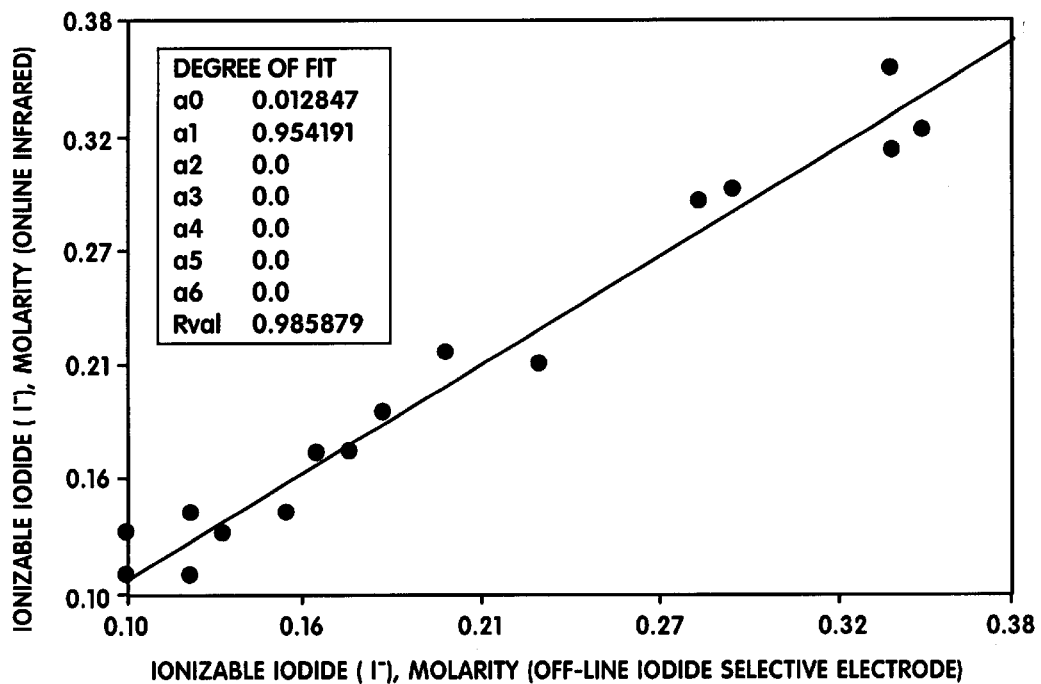
FIG. 5A is a correlation plot of analytical concentration values predicted by on-line infrared vs. analytical concentration values predicted by off-line iodide selective electrode for ionizable iodide ($I^-$)
Figure 5B:
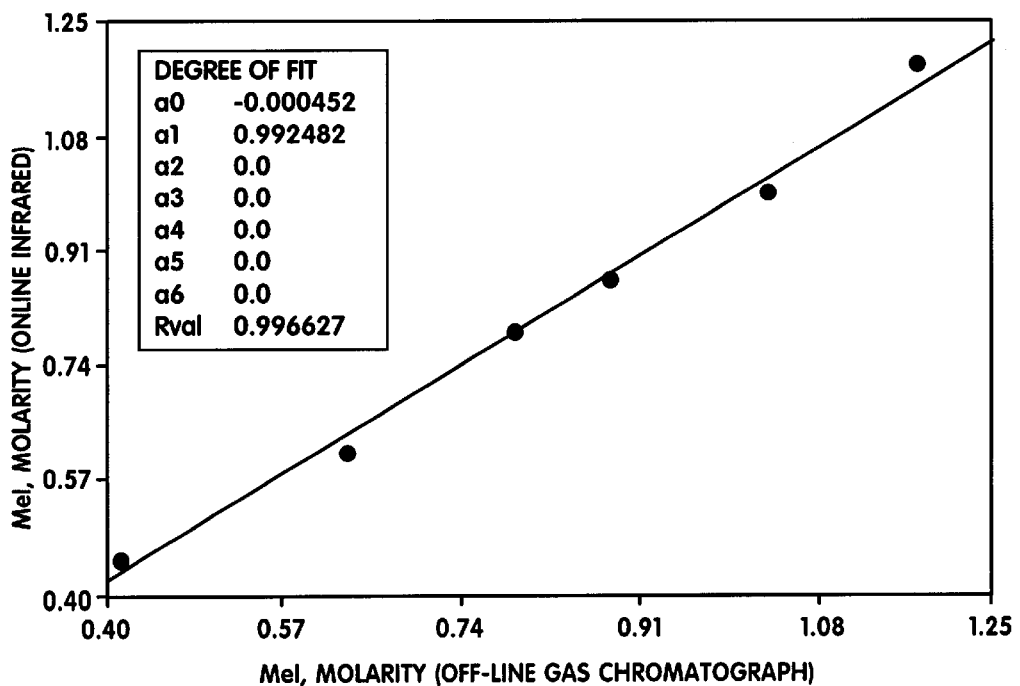
FIG. 5B is a correlation plot of analytical concentration values predicted by on-line infrared vs. analytical concentration values predicted by off-line gas chromotograph for methyl iodide (MeI)
Figure 5C:
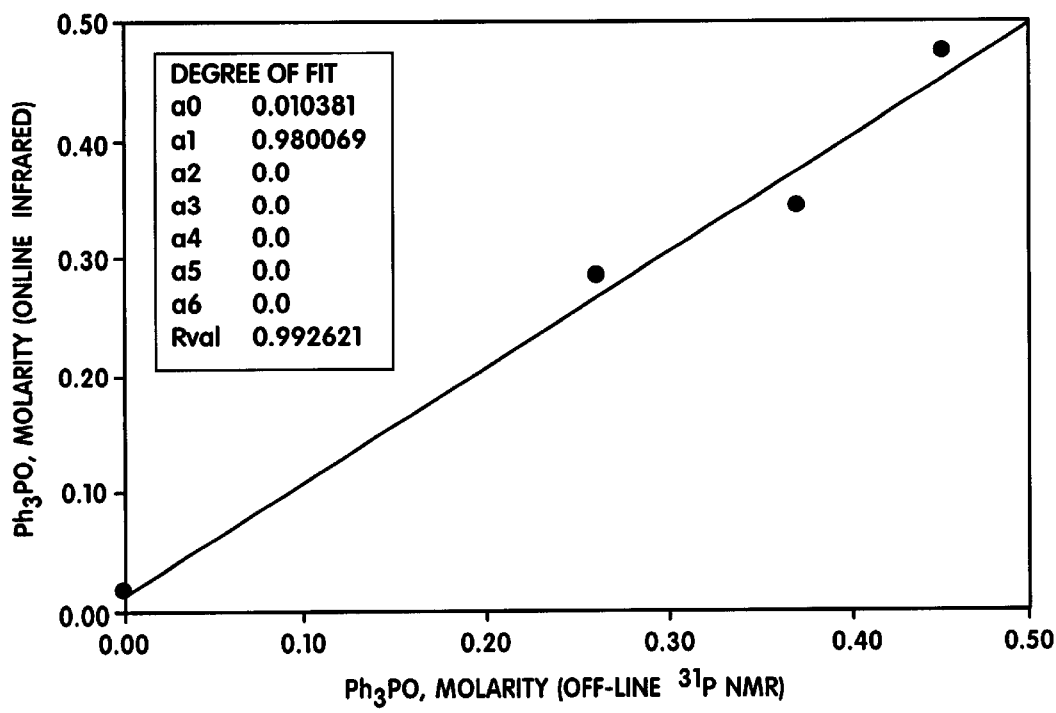
FIG. 5C is a correlation plot of analytical concentration values predicted by on-line infrared vs. analytical concentration values predicted by off-line $^{31}P$ NMR for triphenyl phosphine oxide ($Ph_3PO$)
Figure 5D:
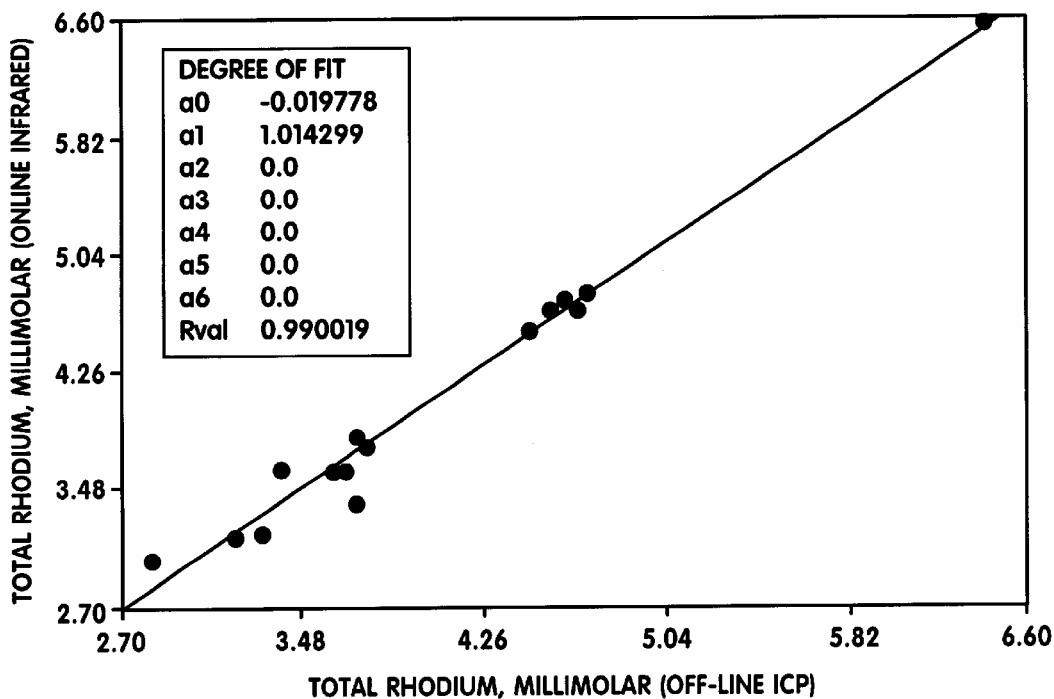
FIG. 5D is a correlation plot of analytical concentration values predicted by on-line infrared vs. analytical concentration values predicted by off-line inductively coupled plasma spectroscopy (ICP) for rhodium.
Figure 5E:
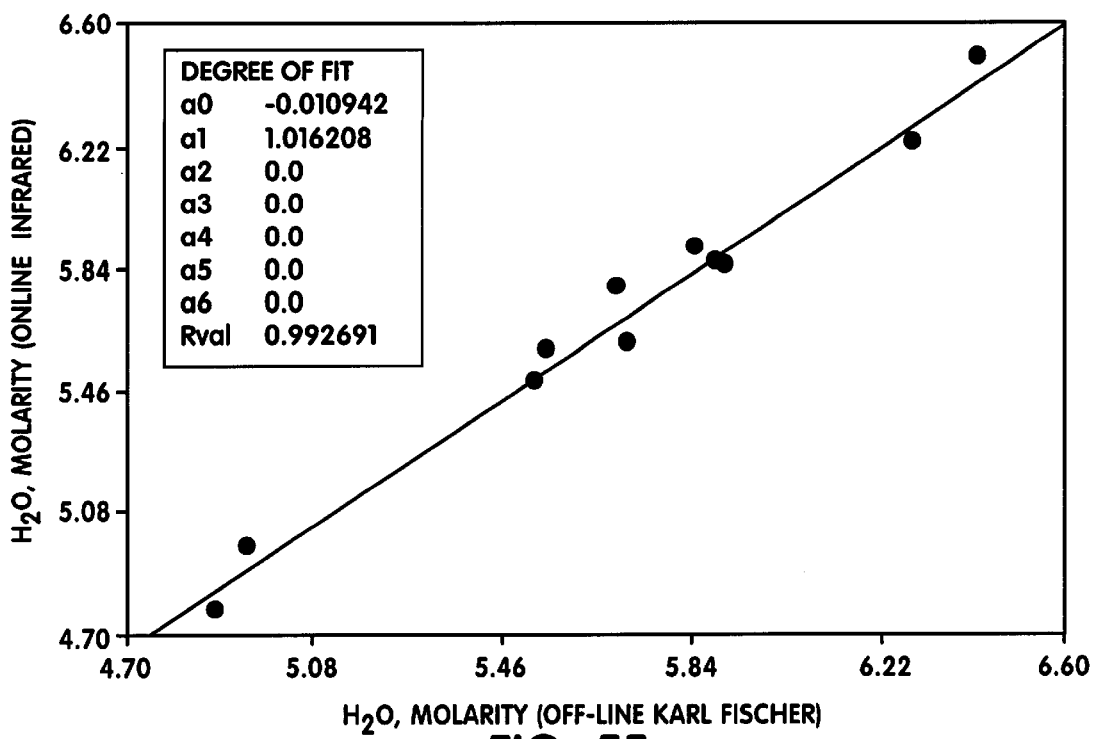
FIG. 5E is a correlation plot of analytical concentration values predicted by on-line infrared vs. analytical concentration values predicted by off-line Karl Fischer analysis for water.
Figure 5F:
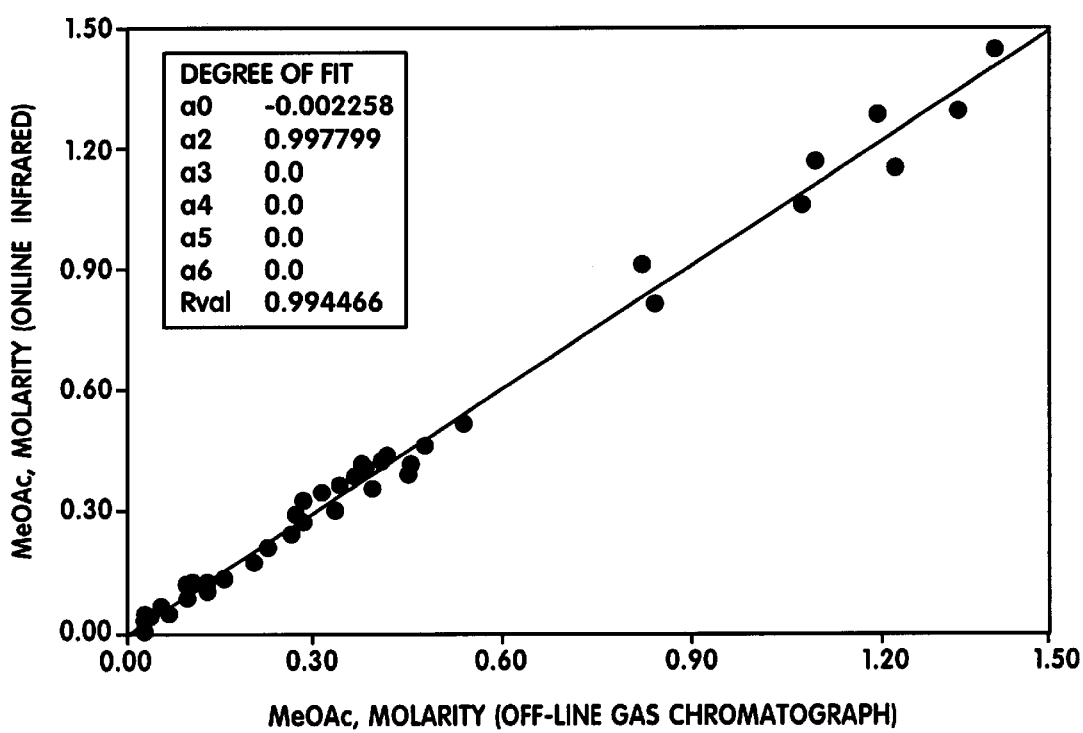
FIG. 5F is a correlation plot of analytical concentration values predicted by on-line infrared versus analytical concentration values predicted by off-line gas chromatography for methyl acetate.
Figure 10B:
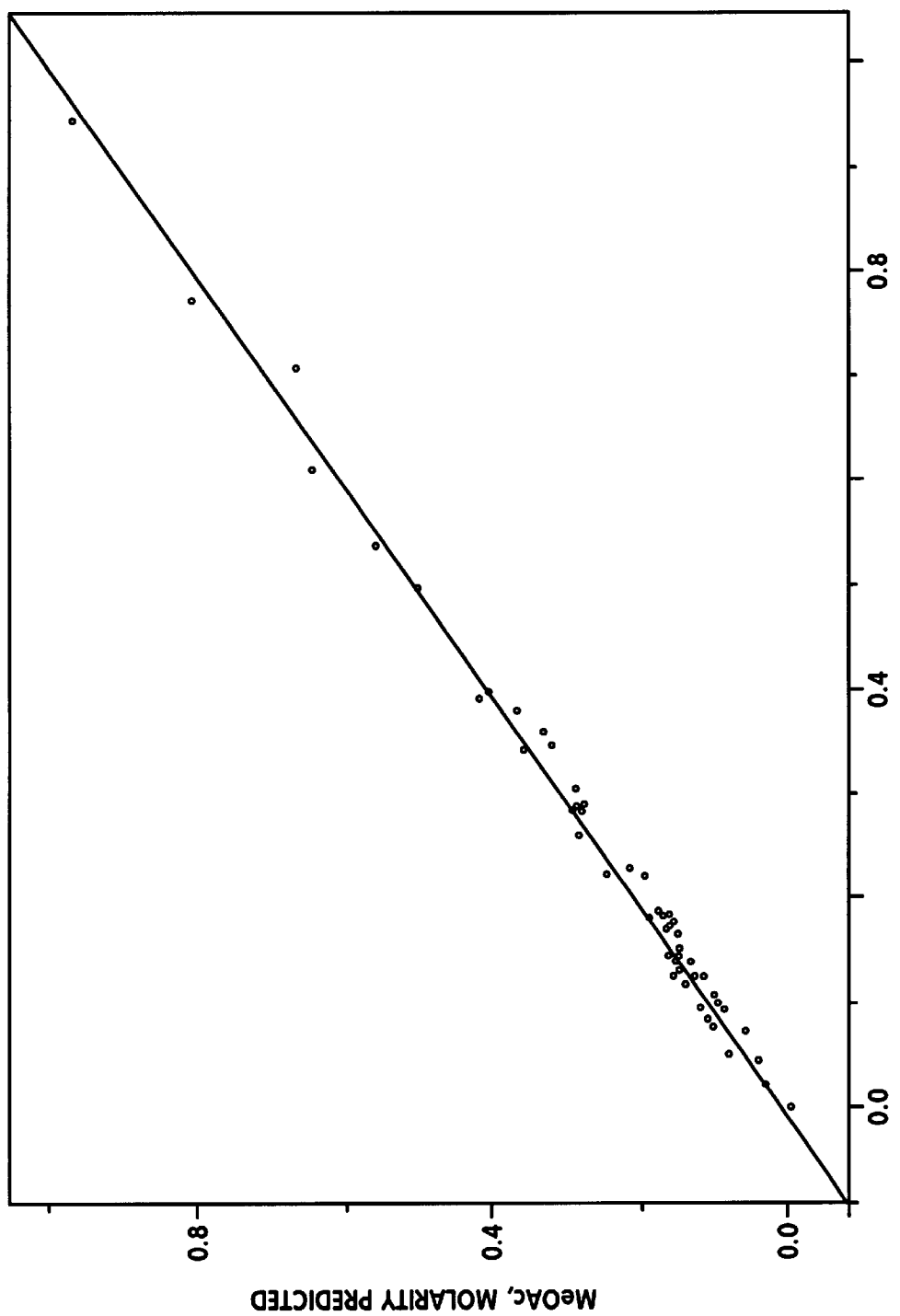
FIG. 10B is a calibration curve for methyl acetate generated from modeling of the spectroscopic data in FIG. 8.

FIG. 10B shows the calibration curve generated by the modeling software and associated with FIG. 10A. Excellent correlation is observed over the total methyl acetate range of 0–1.0 molar. This calibration model was validated as shown in Table 4 and FIG. 4 and was used to correlate the gas chromatographic values for actual reactor samples as shown in FIG. 5F.

Example 2

Figure 11:
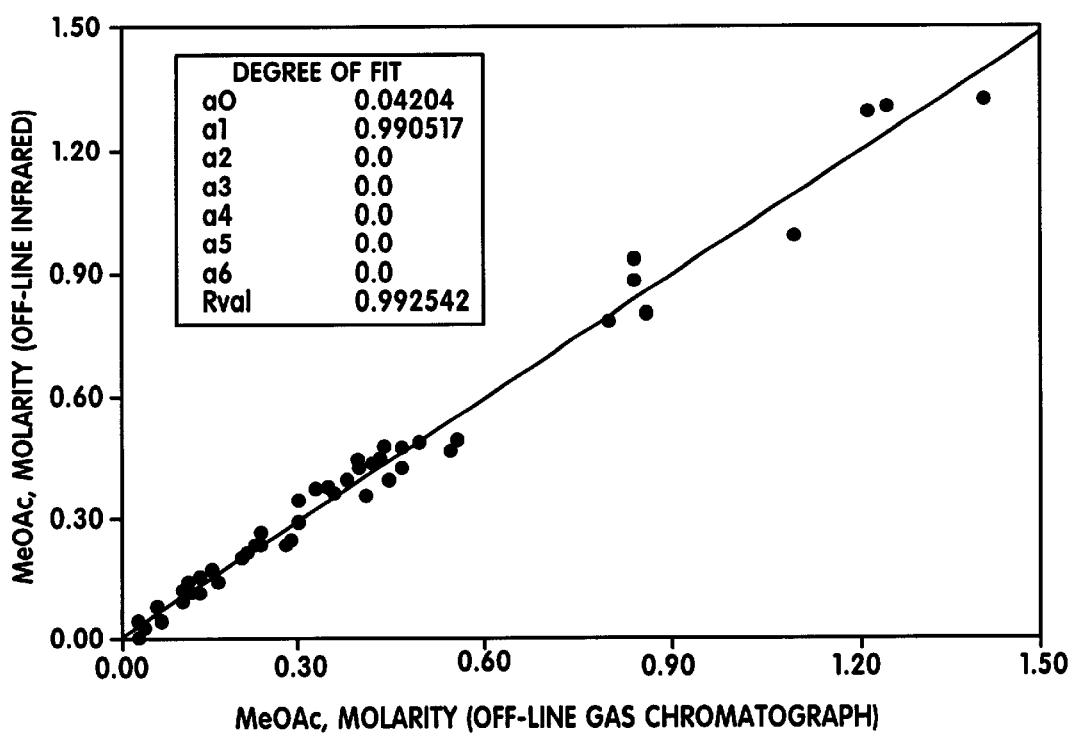
FIG. 11 is a correlation plot of analytical concentration values predicted by laboratory extended mid-infrared versus analytical concentration values predicted by off-line gas chromatography for methyl acetate.

The sixty calibration solutions described in Example 1 were also run on a laboratory infrared analyzer at room temperature and pressure, with similar transmission cell and detector set up as described above in Example 1. The resulting off-line model was also used to correlate the gas chromatographic values for reactor samples described in Example 1. The resulting plot in FIG. 11 again shows excellent correlation with an R factor of 0.993. This demonstrates the power of the infrared method of analysis in either off-line or on-line mode.

Example 3

Using the general approach outlined in Example 1, a laboratory infrared calibration model was created from spectral data obtained at room temperature and pressure using a 0.012 mm pathlength transmission cell with zinc selenide (ZnSe) windows. The use of a short pathlength allows access to the fingerprint region of the mid-infrared. This region is approximately 1800 to 400 cm$^{-1}$. In the case of the 0.5 mm pathlength cell used in Example 1, residual acetic acid absorbances are too strong to allow component quantitation in this fingerprint region. Furthermore, the working range of the InAs detector necessary in Example 1 to provide sufficient sensitivity in the extended mid-infrared region does not extend into the fingerprint region. Thus a TGS detector was used in studies involving the fingerprint region. As sapphire windows absorb significant radiation themselves below 1600 cm$^{-1}$, ZnSe windows were used.

Figure 12:
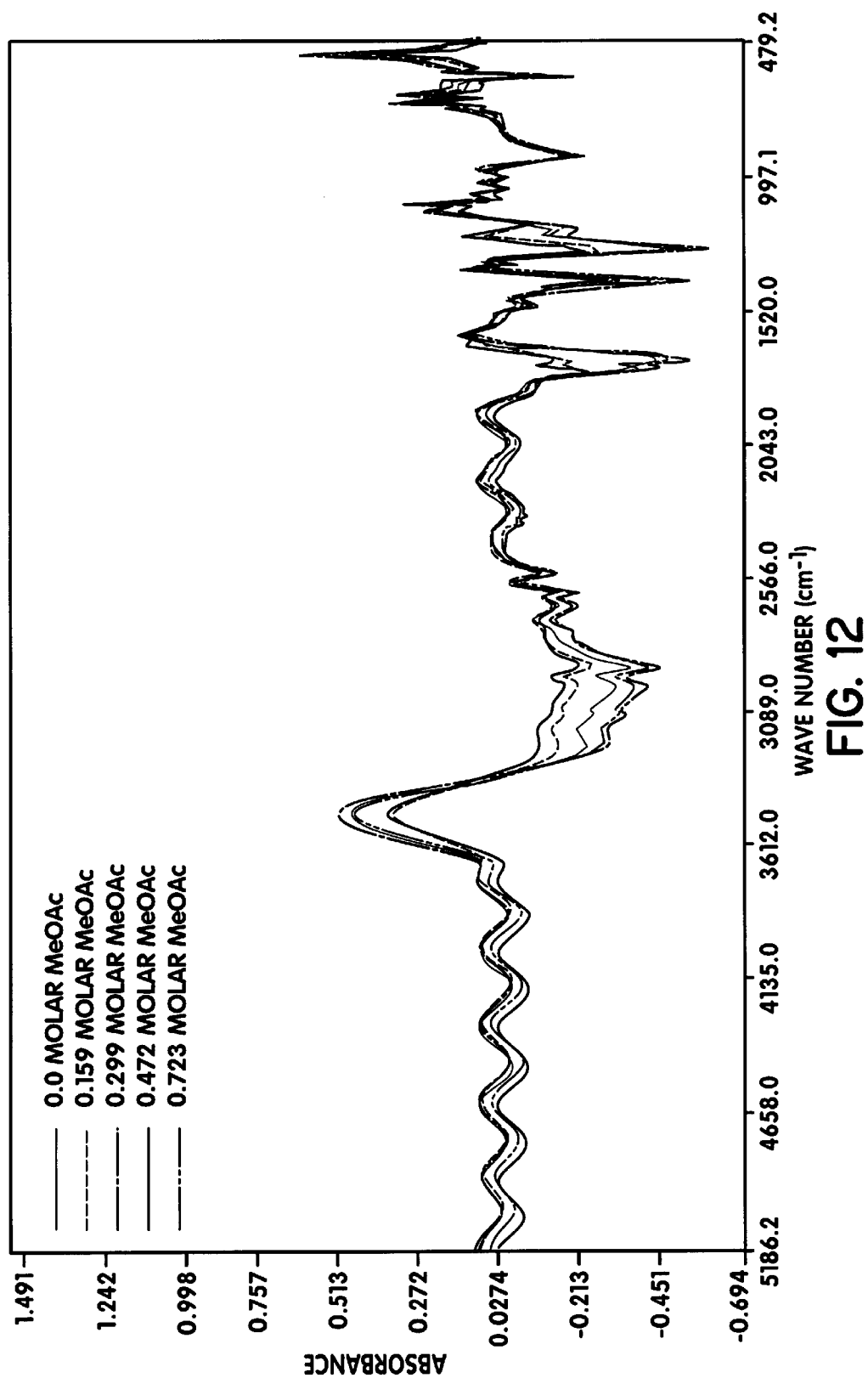
FIG. 12 is an overlay of laboratory mid-infrared spectra of calibration solutions obtained with a 0.012 mm transmission cell.

Several overlaid spectra are shown in FIG. 12. These spectra represent methyl acetate concentrations from 0 to 0.72 molar. A total of 50 such calibration spectra were obtained from 50 calibration solutions. As in Example 1 above, all solutions were multi-component and an acetic acid reference spectrum was subtracted from each sample spectrum. A particular feature of FIG. 12 must be noted. The wave pattern evident from about 5400 to 3500 cm$^{-1}$ is not associated with solution component absorption but rather with a phenomenon called interference fringing. This effect, well known to those skilled in the art of spectroscopy, is a feature of transmission cells of particularly short pathlength. It is due to reflection of significant portions of the incident infrared radiation between the cell windows rather than transmission. As the resulting wave pattern contributes to the substructure of the whole spectrum, it acts as an interferant in solution component calibration and quantitation.

Figure 13:
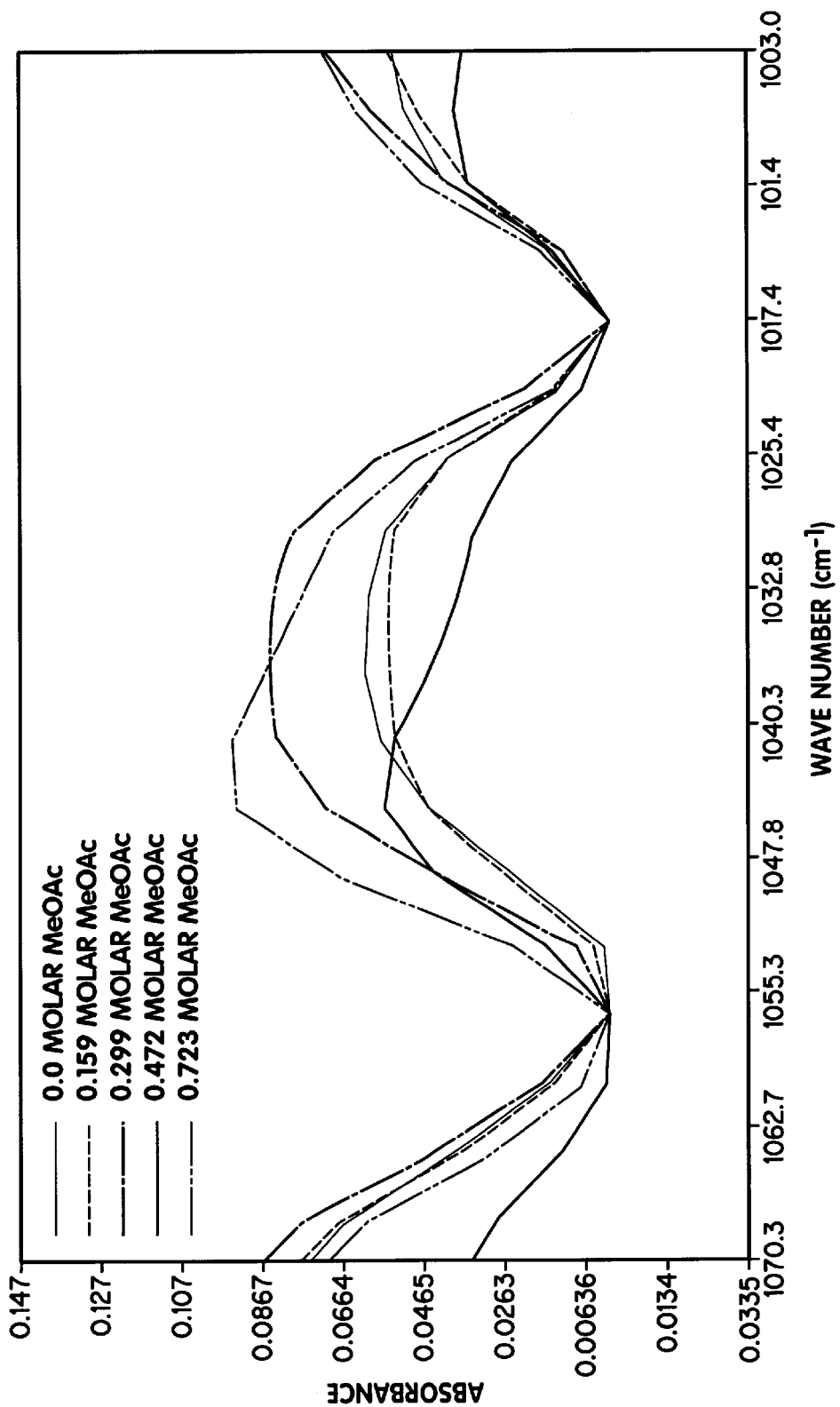
FIG. 13 is an expanded view of FIG. 12 where a portion of the fingerprint region around 1050 $cm^{-1}$ is associated with methyl acetate absorption.
Figure 14A:
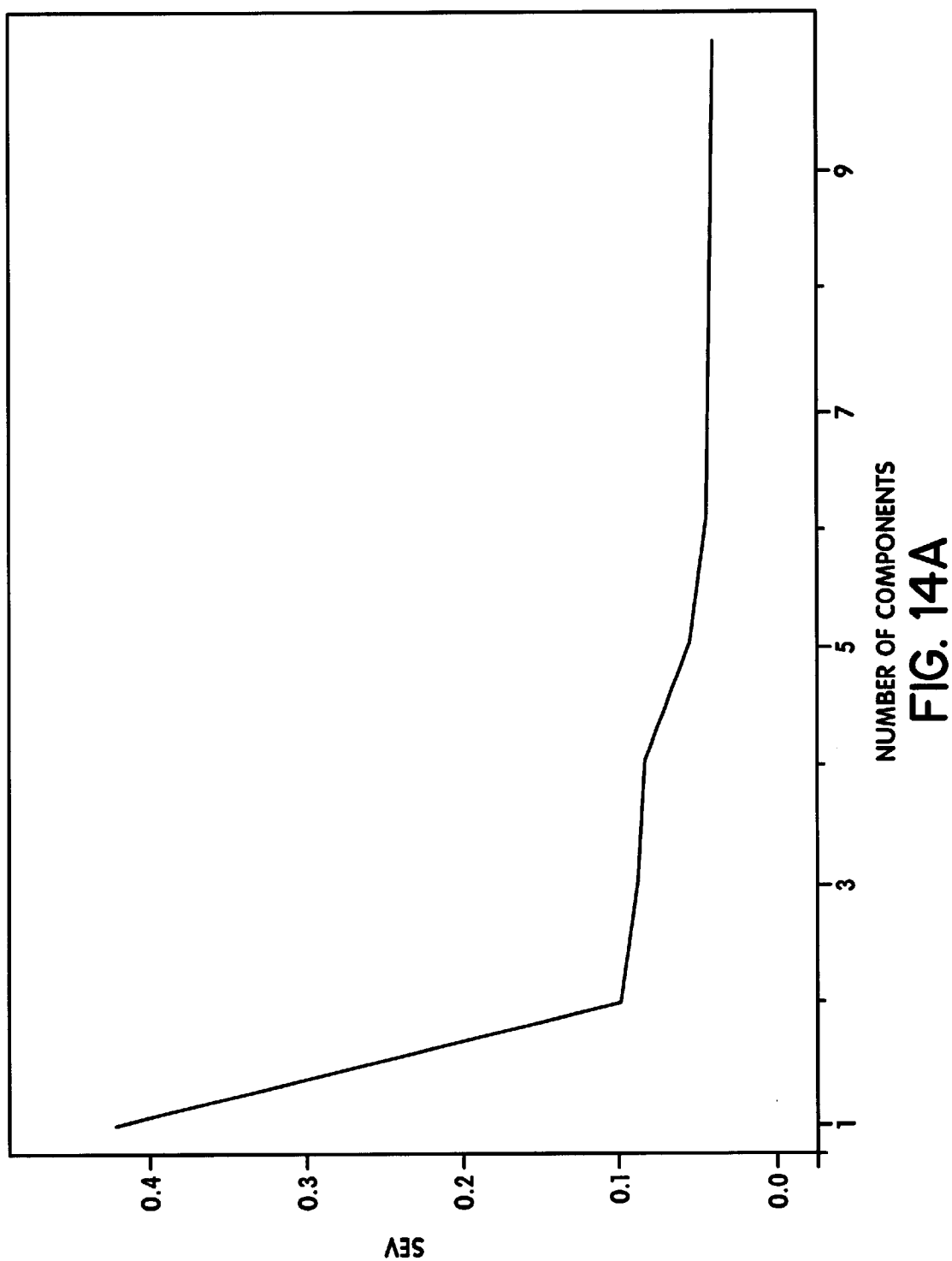
FIG. 14A is a cross validation plot generated by PIROUETTE™ for methyl acetate from the spectroscopic data obtained in FIG. 12.
Figure 14B:
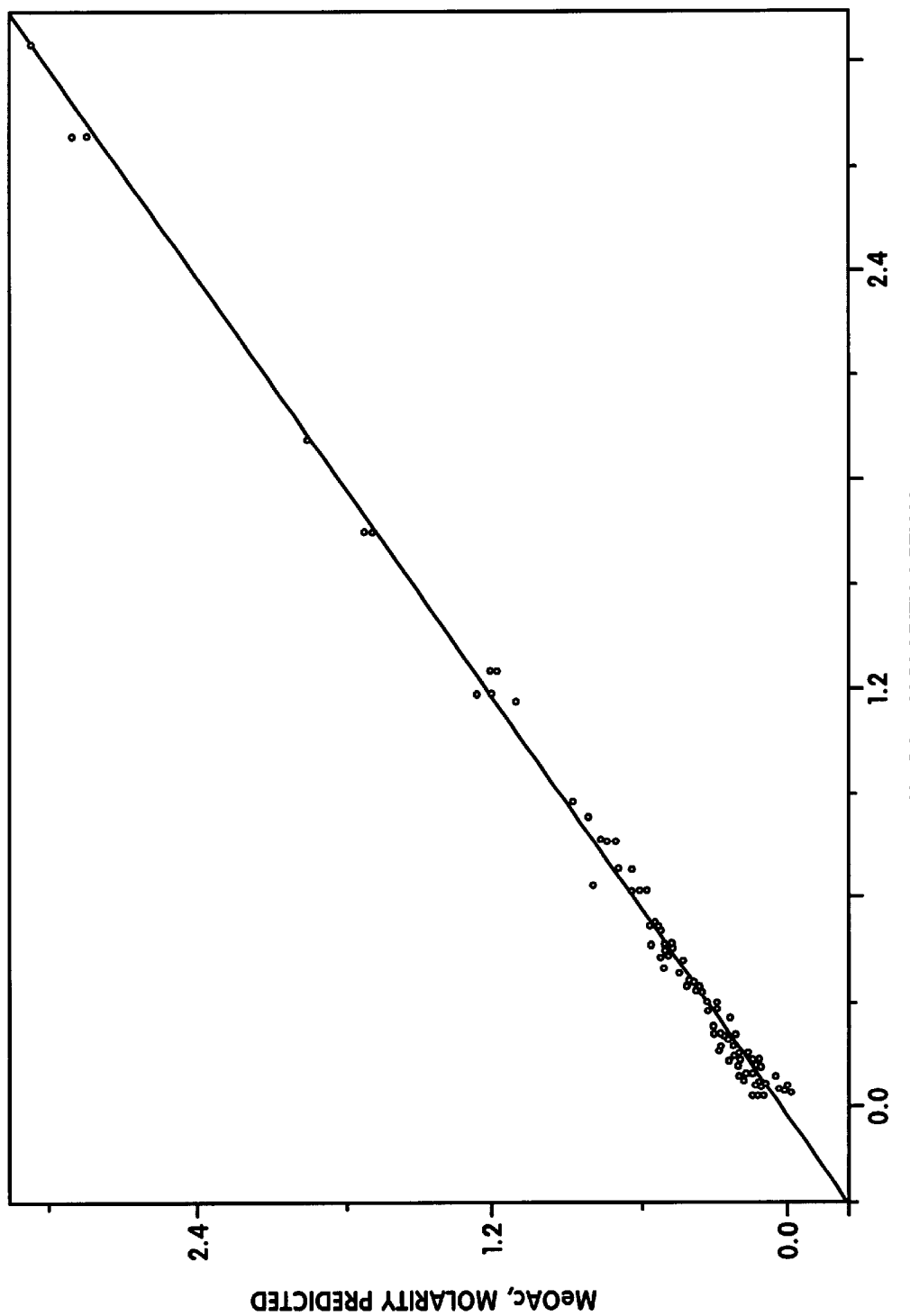
FIG. 14B is a calibration curve for methyl acetate generated from modeling of the spectroscopic data in FIG. 12.

Initial exploratory analysis of the spectral data by PIROUETTE™ showed that substantial relevant information regarding methyl acetate was contained in a few broad overlapping bands around 1050 cm$^{-1}$. This information may be associated with CO stretching unique to the ester linkage in methyl acetate. The region around 1050 cm$^{-1}$ from FIG. 12 is expanded in FIG. 13 to more clearly show the area of interest. Visually, no discernable pattern of increasing intensity with increasing methyl acetate was evident, but chemometric analysis allowed changes masked by interferences to be detected. The SEV calibration and plot curve are illustrated in FIG. 14A and FIG. 14B. The minimum SEV in FIG. 14A reflects an accuracy of about ±0.05 molar for predictions by this model. This accuracy is decreased compared to Example 1 and relates to the use of the 0.012 mm cell.

Figure 15:
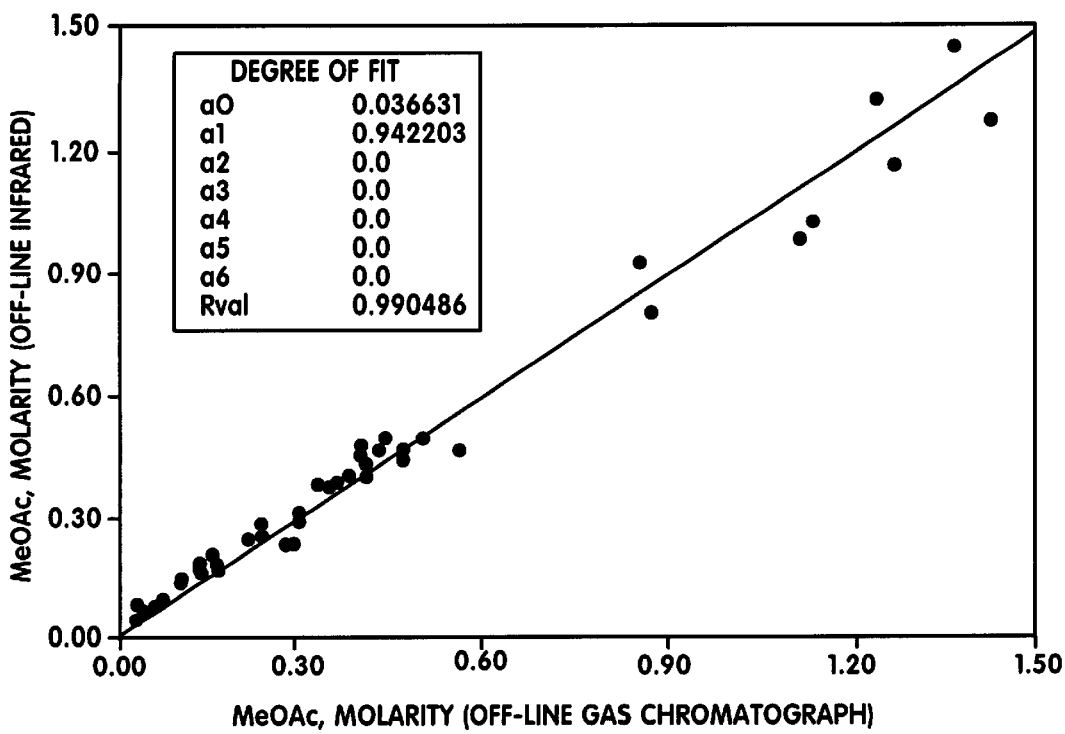
FIG. 15 is a correlation plot of analytical concentration values predicted by laboratory fingerprint mid-infrared versus analytical concentration values predicted by off-line gas chromatography for methyl acetate.

This off-line model was used to correlate the gas chromatographic values of reactor samples as described in Example 1. Excellent correlation is again evident between the two analytical techniques as shown in FIG. 15. The R factor for this cell of 0.990 is slightly lower than for the cell in Example 1 relating to the use of the short pathlength transmission cell.

Example 4

Another method for determining methyl acetate in reactor solutions is to employ an Attenuated Total Reflection (ATR) probe. The ATR method is well known to those skilled in the spectroscopic art and involves contacting the solution with a crystal rod of suitable material; i.e., ZnSe. The internal reflection of the incident infrared radiation through the crystal to the reactor solution provides a means of producing an absorption spectrum of the material. The effect is to generate a short pathlength without the interference fringing problems inherently associated with short pathlength cells. Use of the ATR probe provides an alternate means of examination of the fingerprint region of the infrared spectrum, which is approximately 1800 to 400 cm$^{-1}$.

Figure 16:
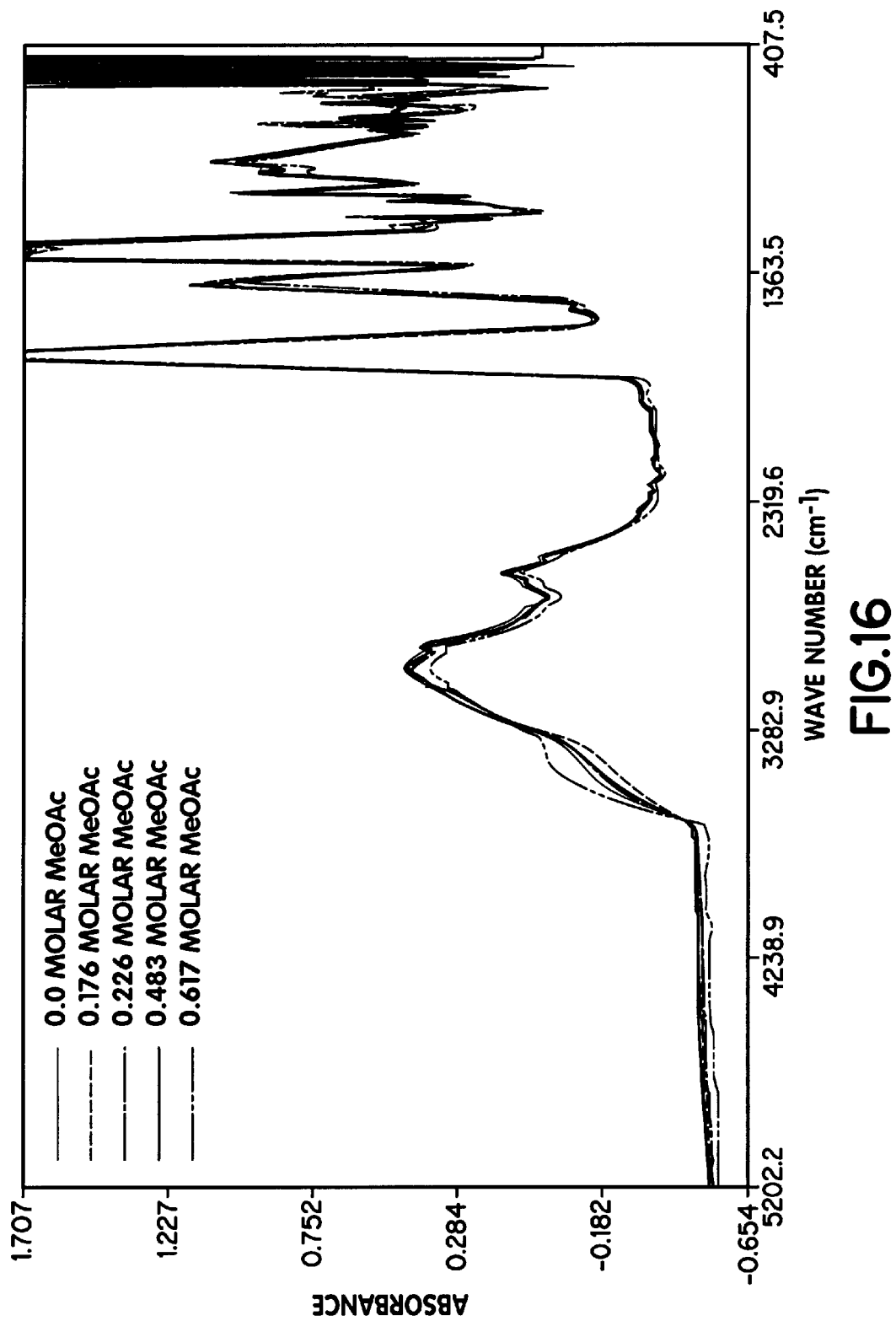
FIG. 16 is an overlay of laboratory mid-infrared spectra of calibration solutions obtained with an ATR cell containing a zinc selenide crystal.
Figure 17:
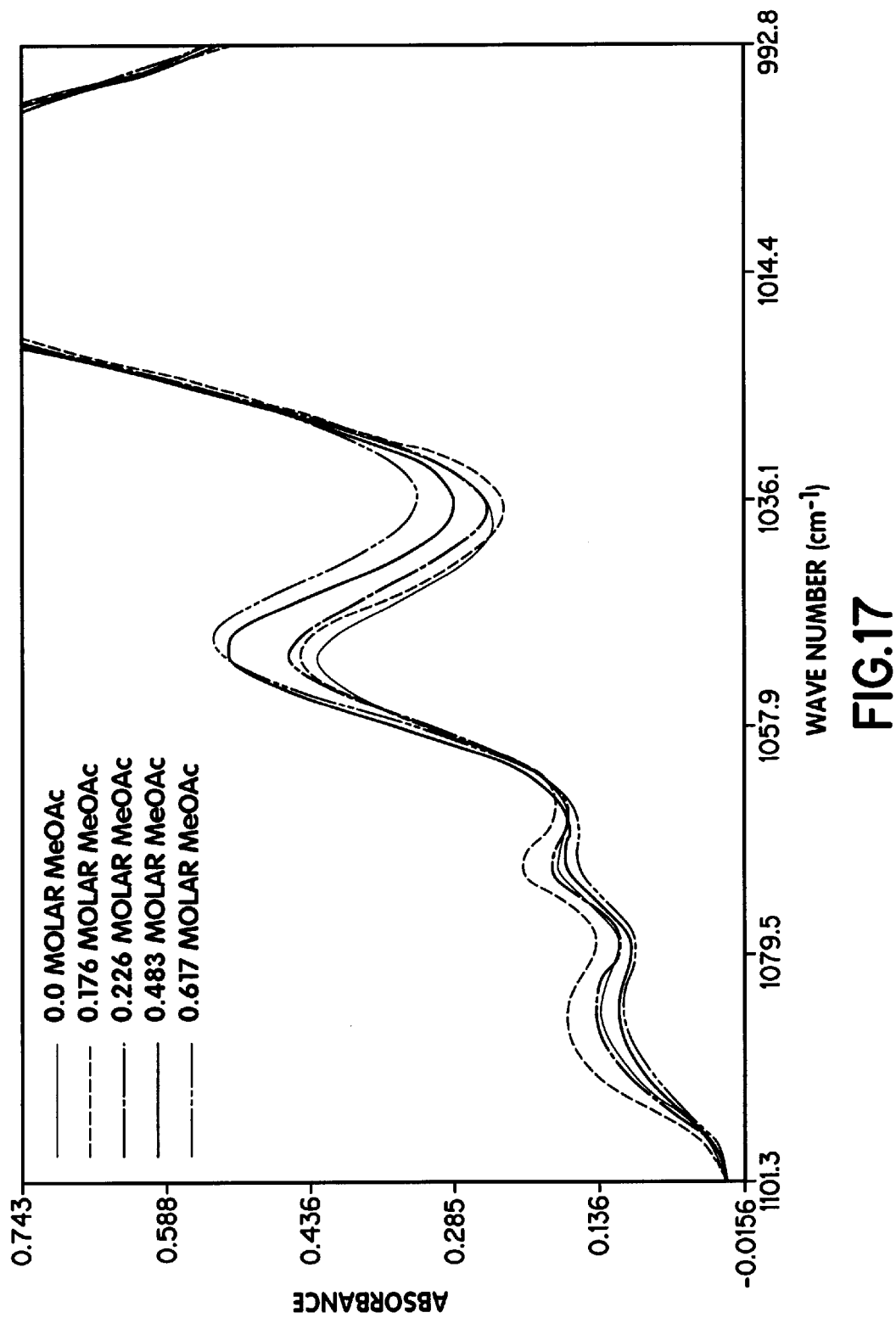
FIG. 17 is an expanded view of FIG. 16 where a portion of the fingerprint region around 1050 $cm^{-1}$ is associated with methyl acetate absorption.
Figure 18A:
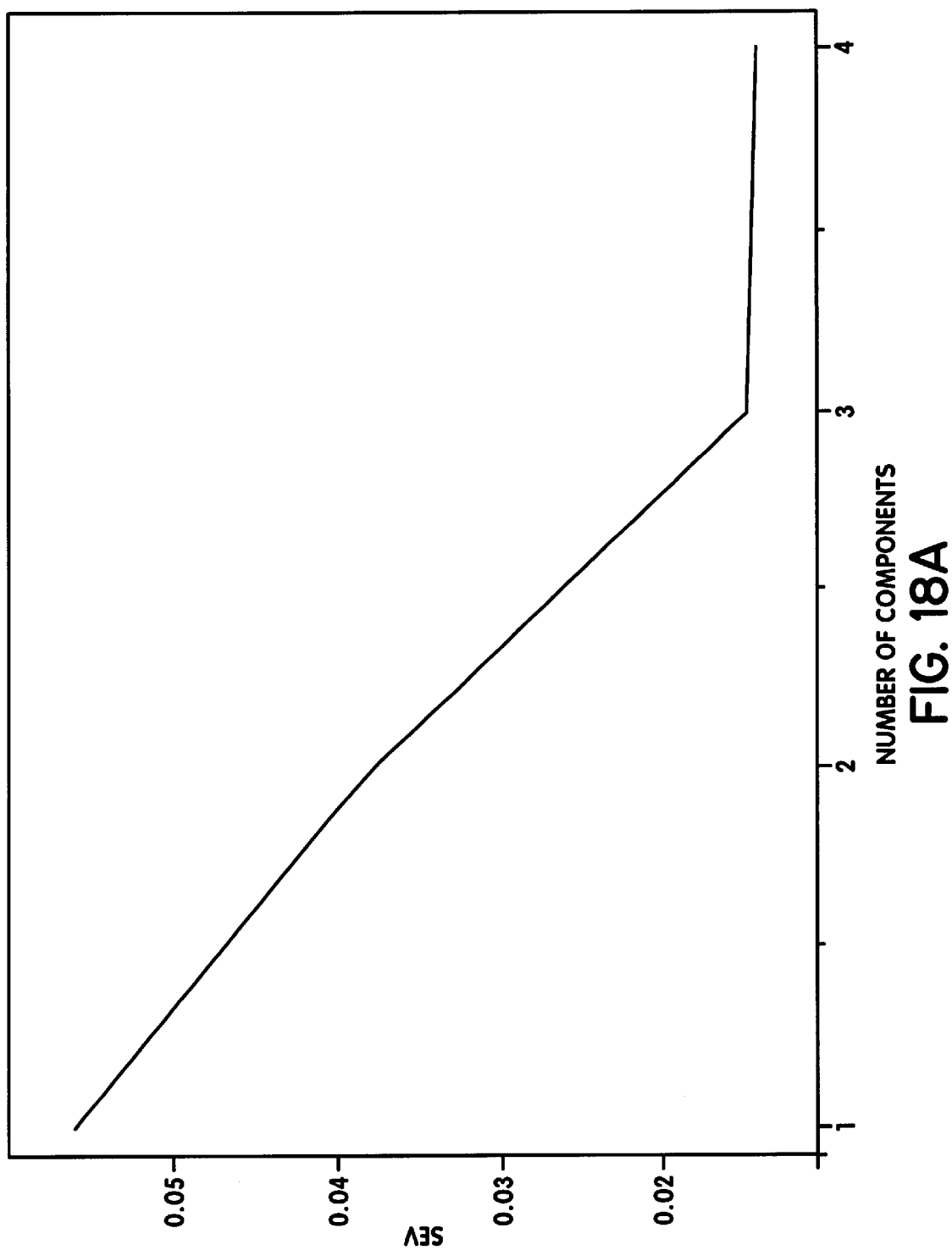
FIG. 18A is a cross validation plot generated by PIROUETTE™ for methyl acetate from the spectroscopic data obtained in FIG. 16.
Figure 18B:
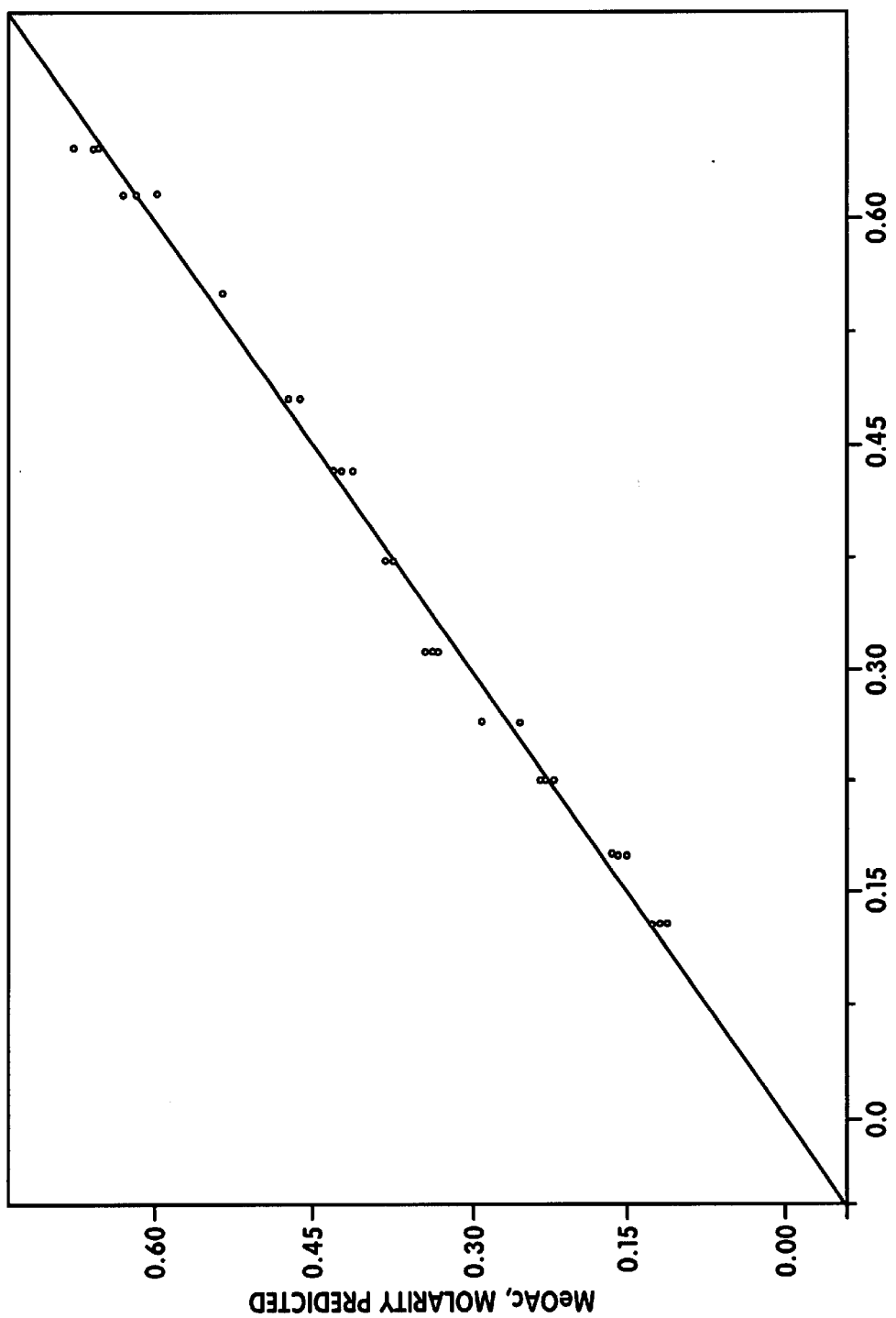
FIG. 18B is a calibration curve for methyl acetate generated from modeling of the spectroscopic data in FIG. 16.

A one inch diameter, nine reflection, ZnSe probe from Axiom Analytical was used in combination with a TGS detector to analyze twelve multi-component solutions with component concentration ranges similar to those outlined in Example 1 above. Several overlaid spectra in FIG. 16 show the absence of interference fringing which was present in the transmission cell spectra in FIG. 12. The region around 1050 cm$^{-1}$ from FIG. 16 is expanded in FIG. 17 to more clearly show the area of interest. A pattern of increasing intensity with increasing methyl acetate concentration is evident for a broad non-gaussian peak centered around 1050 cm$^{-1}$. An SEV plot and calibration curve for these twelve solutions are shown in FIGS. 18A and 18B. It is clear from these plots that ATR can be used for analyzing methyl acetate, as the SEV plot indicates that an accuracy of ±0.01 molar can be expected.

Example 5

A continuous 2 liter bench scale reactor was run for several days under the conditions set out below:

Reactor temperature=187° C.–189° C.

Reactor pressure=400 psig (130 psig CO)

Methyl iodide concentration=1.0 molar

Water concentration=3.5 molar

Rhodium concentration=6.5 millimolar

Triphenyl phosphine oxide concentration=0.5 molar

Methanol feed rate=320 g/hr.

The process was automatically controlled from data generated by an on-line infrared analyzer. The analyzer used in this example was a single source, dual detector, dual cell model and was comprised of a sample compartment and an electronics compartment. The sample compartment contained the cells, tubing to allow reactor solution to flow through the cells, a flowmeter, filter and heater. All parts in contact with process solution were fabricated from Hastelloy™ B2. The electronics compartment contained the single polychromatic infrared light source, the interferometer, the detectors, analog input and output cards, and associated peripherals such as power supply, and other components which control the analyzer. The two compartments were connected via infrared transparent windows which allowed light to pass from the source, through the cells and back to the detectors.

Reactor solution flowed continuously through the analyzer and was returned to the reaction system via the low pressure flash tank. Mid- and extended mid-infrared analyses were sequentially carried out using a 0.075 mm pathlength cell and a 2 mm pathlength cell, respectively. Infrared light passing through the mid-infrared cell was deflected to a deutero triglycine sulfide (DTGS) detector and light passing through the extended mid-infrared cell was deflected to an indium arsenide (InAs) detector. Sapphire windows were used in both cells and the sample cabinet was maintained at a temperature of 100° C.

The same 2 liter bench scale reactor and the same on-line infrared analyzer as discussed herein in Example 1 were used for all subsequent examples discussed herein.

Figure 19:
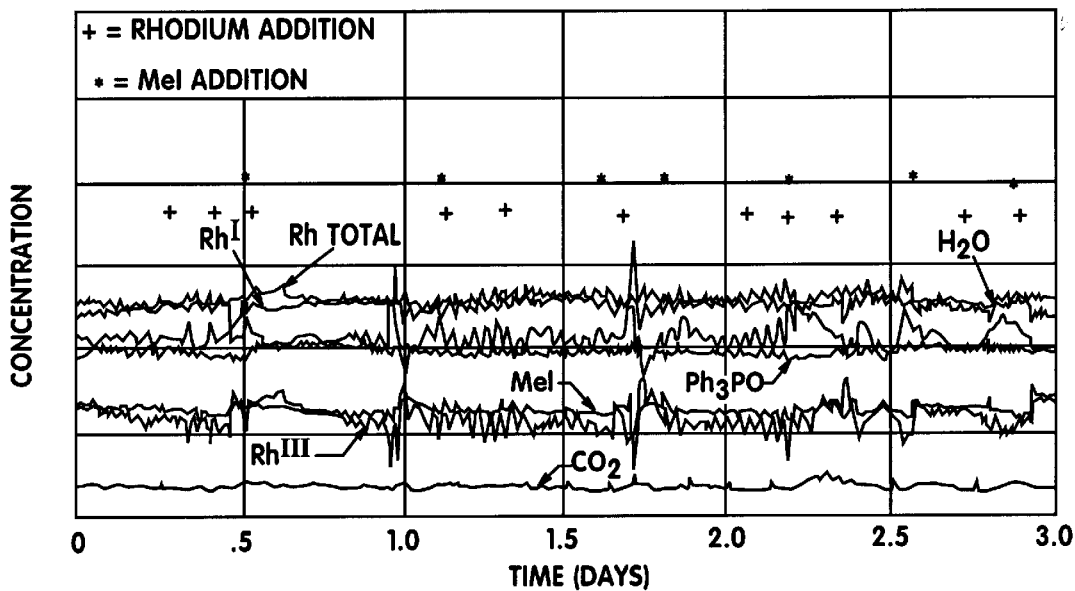
FIG. 19 is a multi-component trend file containing three days of run time data for seven reactor solution components.

A multi component trend file containing three days of run time data is shown in FIG. 19. The concentrations of seven reactor solution components are trended in this chart. Each of the seven trend lines is composed of more than 2000 data points. No concentration values are given on the Y axis, as each reactor solution component has its own scale. FIG. 19 is merely representative of the trends for each component. Also plotted on this chart are the times at which methyl iodide (MeI) and rhodium were added. The method of controlling component addition for rhodium and methyl iodide was slightly different than the method for controlling the addition of water. Rhodium and methyl iodide are not formally consumed in the process, but some losses did occur because of precipitation of rhodium and because of losses downstream of the reaction section for both rhodium and methyl iodide. Water, on the other hand, is consumed in the process by the water gas shift reaction.

The component concentrations measured by the analyzer were converted to proportional 4–20 mA signals. Component addition was then controlled by a Process Logic Controller (PLC) based on these signals. Signals were sent to the PLC every 2 minutes averaged over the life of the run, but the concentration was evaluated as a rolling average over a one hour time period. In the case of rhodium or methyl iodide, if the average molar (or millimolar) concentration value over the rolling time period fell below the preset control limits set out below, a volume sufficient to return the component to its normal control limit of rhodium solution or methyl iodide was automatically added to the system. As water was rapidly consumed in the process, no rolling time period was used. Instead, a water pump operated continually and the pump rate was automatically adjusted in response to every data point to maintain water within preset control limits. The lower control limits used in this example are shown below in Table 5. The reaction consumes the analyzed reactant components over time, and thus upper control limits are not required. Over the three day test period it was not necessary to add triphenyl phosphine oxide.

TABLE 5

| COMPONENT | NORMAL CONTROL LIMIT | LOWER CONTROL LIMIT |
|---|---|---|
| Water | 3.5 molar | 3.2 molar |
| Methyl Iodide | 1.0 molar | 0.9 molar |
| Rhodium | 6.5 millimolar | 6.0 millimolar |
| Ph$_3$PO | 0.50 molar | 0.45 molar |

It should be noted that the use of an average concentration and the generous control limits are not solely a function of precision and accuracy of the analyses. In a reaction system of this kind in which there is continual cycle of solution between the reactor and flash tank, the solution component concentration may not be at steady state in either vessel. The use of a rolling time average thus allows for these effects to be buffered and prevents unnecessary component additions.

It can be seen from FIG. 19 that use of infrared analyzer data allowed excellent process control. Only two sharp spikes were observed over the three-day period which are believed to have been caused by momentary electronic noise. Reaction rate is a direct function of the concentration of rhodium, methyl iodide, H$_2$O and (when present) triphenyl phosphine oxide. The ability to continuously monitor and tightly control concentrations of these components in the reactor allows productivity to be maximized, system upsets to be identified quickly and addressed, and rhodium precipitation to be minimized. In addition, a tight control of reactor water concentration results in acetic acid product with a minimal variation in water content, in turn resulting in more stable operation of the dryer column to remove water from the acetic acid.

Figure 20:
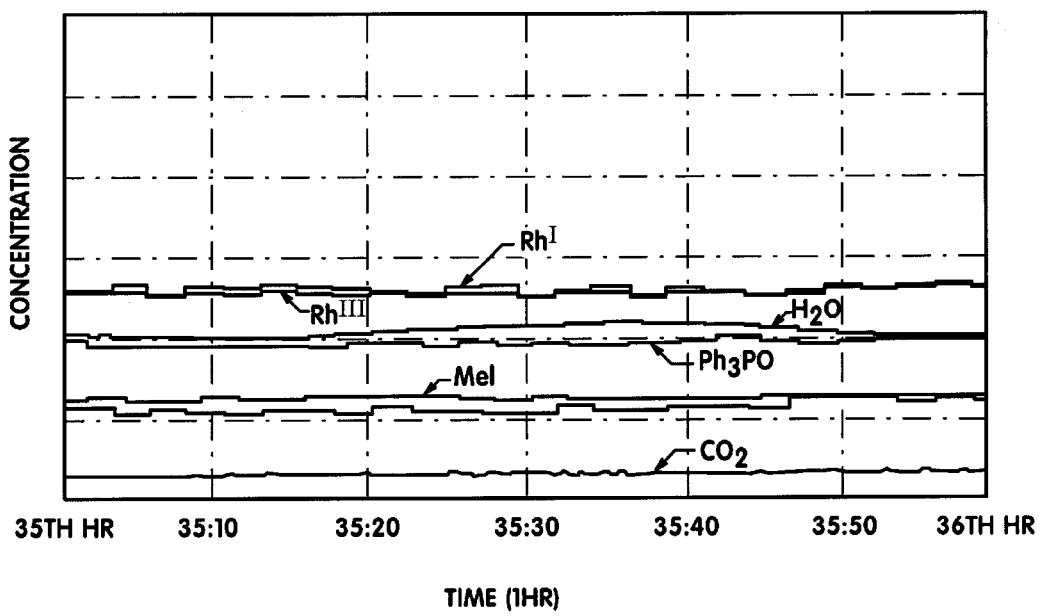
FIG. 20 is an expanded view of a one hour time segment of the trend file of FIG. 7.

FIG. 20 shows an expanded version of FIG. 19 in which a one-hour time segment (the 35$^{th}$ hour of the three day run) of the reaction is represented. This particular segment was chosen because it contains no component additions (other than water) and because it represents a period of very stable operation when reactor level was under very tight control. Thus, any data scatter in this period should predominately reflect measurement precision. The highest and lowest concentrations for the seven components on this trend chart for the one-hour period (30 data points) are shown below in Table 6.

TABLE 6

| COMPONENT | HIGH | LOW |
|---|---|---|
| Rh$^I$ | 4.46 | 4.40 |
| Rh$^{III}$ | 1.91 | 1.96 |
| Rh total | 6.62 | 6.60 |
| Triphenyl Phosphine Oxide | 0.50 | 0.49 |
| Water | 3.48 | 3.27 |
| CO$_2$ | 5.40 | 5.31 |
| Methyl iodide | 1.03 | 1.03 |

Example 6

The form of rhodium, i.e. Rh(CO)$_2$I$_2^-$ (Rh$^I$) or Rh(CO)$_2$I$_4^-$ (Rh$^{III}$) and the stability of rhodium to precipitation in acetic acid reactor solution is a function not only of solution chemical composition, but also of physical variables such as stirring rate. In conventional liquid reactors used by acetic acid manufacturers practicing methanol carbonylation technology, stirring is considered necessary to maintain solution homogeneity. This may be particularly true for dispersion of carbon monoxide in solution, as isolated pockets of reactor solution without sufficient dissolved carbon monoxide may be prone to precipitate rhodium.

In the experiment outlined below, conditions used in the continuous bench scale reaction reactor were as follows:

Temperature=185° C.

Pressure=400 psig

Rhodium=6 millimolar

Water=7 molar

Methyl Iodide=0.8 molar

Triphenyl phosphine oxide=0.0 molar

Methanol feed rate=220 g/hr.

Figure 21:
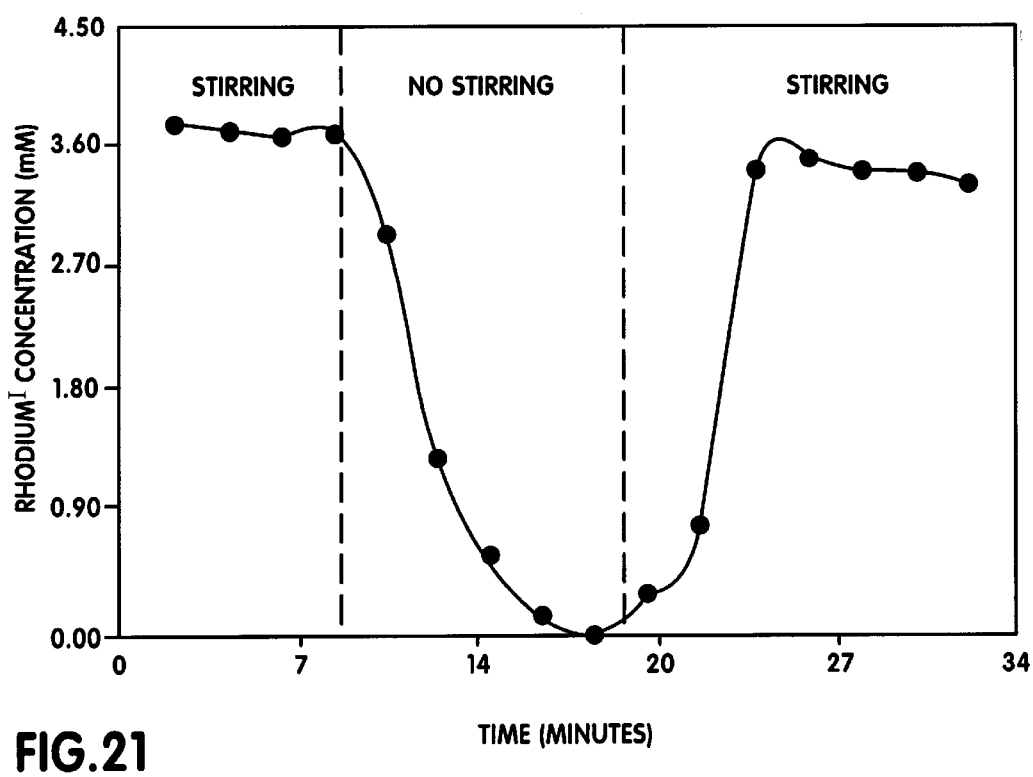
FIG. 21 is a plot of continuous bench scale reactor on-line infrared data for active rhodium species concentration over time as a function of agitation within the reactor solution.
Figure 22:
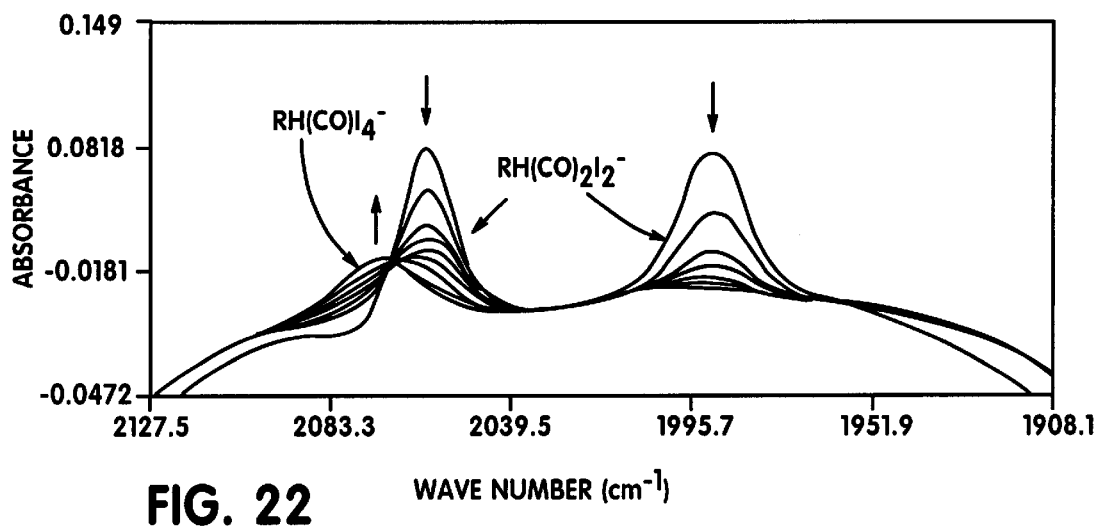
FIG. 22 is an overlay of on-line mid-infrared spectra showing the existence of an inactive species of rhodium, $Rh(CO)I_{4^-}$, in addition to $Rh^I$ as a result of the absence of agitation.

Over the one hour test period, the reactor agitator was turned off one time for several minutes and then back on again to determine the effect on rhodium. It was noted that Rh$^I$ rapidly and completely disappeared in the unagitated solution, but equally rapidly reappeared on reestablishment of agitation as exemplified in FIG. 21. Examination of the analyzer spectra showed that concomitant formation of Rh(CO)I$_4^-$, hereafter referred to as Rh$^{III}$ mono, occurred. Overlaid infrared spectra illustrating the appearance of this species are shown in FIG. 22. The presence of Rh$^{III}$ mono is indicative of carbon monoxide starved conditions. It was shown by manually sampling the reactor and laboratory infrared analysis, that Rh$^{III}$ mono was not forming in the reactor but rather in the transfer lines to the analyzer or in the analyzer itself. This formation was occurring due to continuing reaction (and carbon monoxide consumption without the possibility of replenishment) in the transfer lines. Under normal well-stirred conditions there is sufficient dissolved carbon monoxide in the reactor solution such that Rh$^{III}$ mono does not form in the transfer lines.

This result shows that another advantage of the present invention in terms of process control is the use of on-line infrared analyzer data as a diagnostic tool for stirrer problems or as a tool to optimize agitation rate for various solution compositions and reactor conditions.

Example 7

It has previously been deduced that the form of active rhodium for acetic acid formation is $Rh^I$. In addition, this form is also more stable relative to $Rh^{III}$ in terms of precipitation. Thus there are substantive advantages to be gained in terms of catalyst usage, required catalyst concentration and smooth process operation if a real time knowledge of $Rh^I$ in the acetic reactor can be obtained. Furthermore, the availability of such knowledge allows the effect of changing conditions or of testing new technology on catalyst sensitivity and catalyst form to be rapidly and accurately assessed. Analysis of samples obtained manually from the reactor by the conventional method of elemental analysis or by the method of laboratory infrared analysis described hereinabove, while allowing an accurate determination of total rhodium does not allow the $Rh^I/Rh^{III}$ ratio present in the reactor at time of sampling to be obtained. The methods of elemental analysis such as inductively coupled plasma analysis (ICP) or atomic absorption (AA) are species indiscriminate. Laboratory infrared analysis is capable of distinguishing between and quantifying $Rh^I$ and $Rh^{III}$, but $Rh^I$ rapidly oxidizes to $Rh^{III}$ in traces of air and thus the $Rh^I/Rh^{III}$ ratio measured by this method is rarely representative of the ratio in the reactor at time of sampling. The measured ratio is subject to factors such as time between sampling and analysis, and degree of air contamination on sampling and subsequent handling. Thus the only method of obtaining a knowledge of the $Rh^I/Rh^{III}$ ratio in the reactor is on-line infrared analysis.

Figure 23:
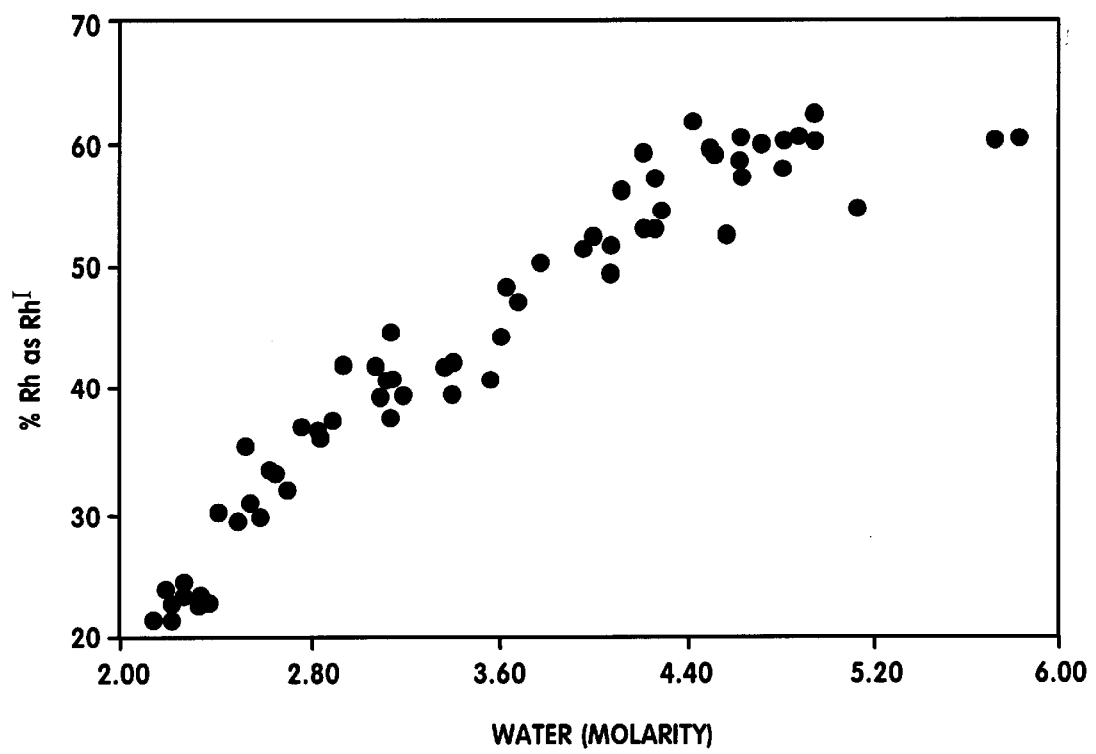
FIG. 23 is a correlation plot of continuous bench scale reactor on-line infrared data for $Rh^I$ concentration as a function of water.

An illustration of the effect of water on $Rh^I$ concentration is shown in FIG. 23. Over a four day period, water was varied from 2 molar to 6 molar under reactor conditions as outlined below. The sampling and analysis frequency was approximately 30 times per hour over the four day period.

Figure 24A:
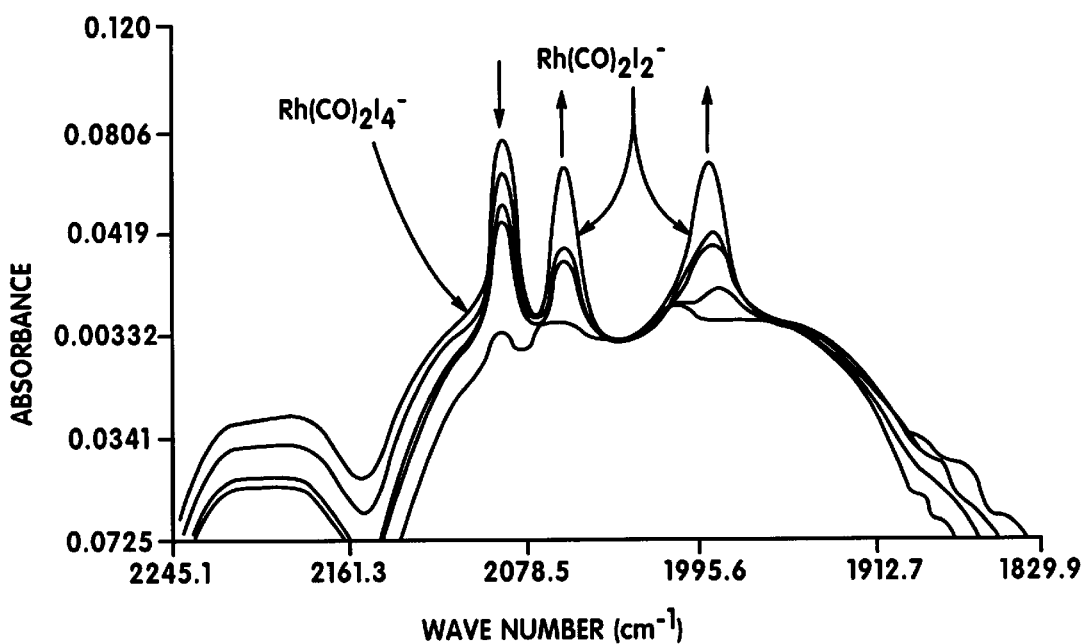
FIG. 24A is an overlay of on-line mid-infrared spectra for rhodium.
Figure 24B:
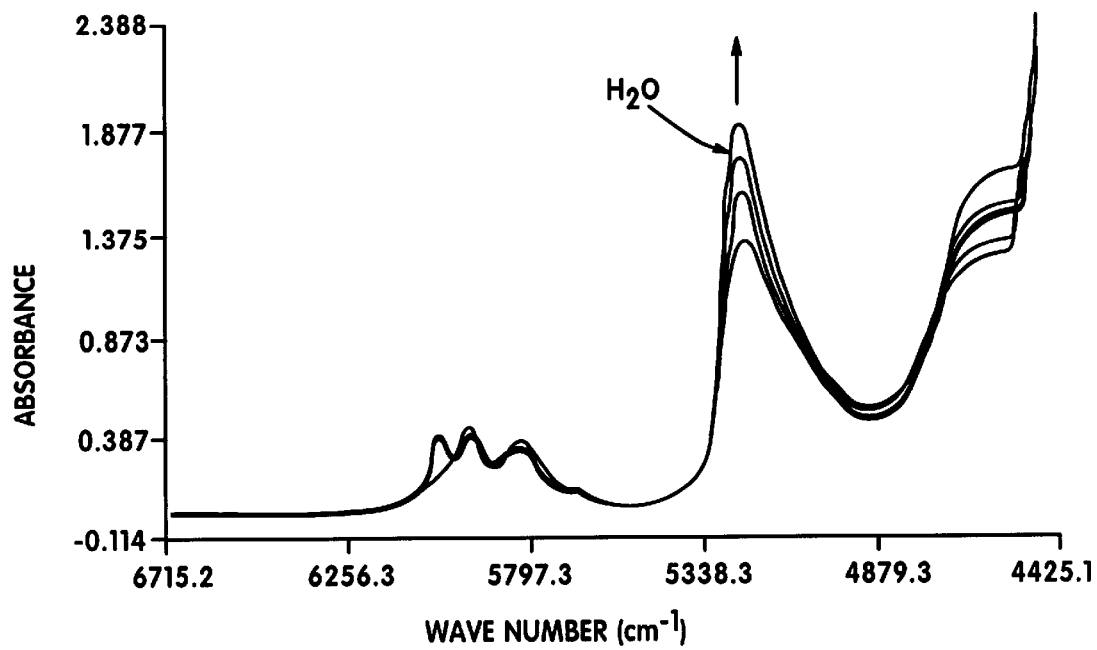
FIG. 24B is an overlay of on-line extended mid-infrared spectra for water.

Temperature=185° C.
Pressure=400 psig
Rhodium=4.8–6.4 molar
Triphenyl phosphine oxide=0.50 molar
Methyl Iodide=0.8 molar
Methanol feed rate=180 g/hr FIG. 23 represents about 60 data points culled from the four days of on-line analyzer run time data. These data points were selected for clarity and are representative of the trend file. The dependence of $Rh^I$ on water is clearly evident. This effect is illustrated spectroscopically in FIGS. 24A and 24B in which overlaid on-line spectra of rhodium in the mid-infrared region and of water in the extended mid-infrared region are presented. The vertical up and vertical down arrows of FIGS. 24A and 24B and subsequent FIGS. show the general increasing and decreasing concentration trends as represented by peak height for each component shown in each FIG. Availability of this kind of data can allow a process to be tailored to achieve optimal balance of methanol feed rate, rhodium consumption and reactor water concentration.

The ability to correlate the concentrations of $Rh^I$ and water shown in this example demonstrates an advantage of the invention. The absolute values of %Rh as $Rh^I$ on the Y axis in FIG. 23 are not optimized, as they are also a function of many other variables such as methanol feed rate, presence of additive mixtures, and the like.

Example 8

Figure 25:
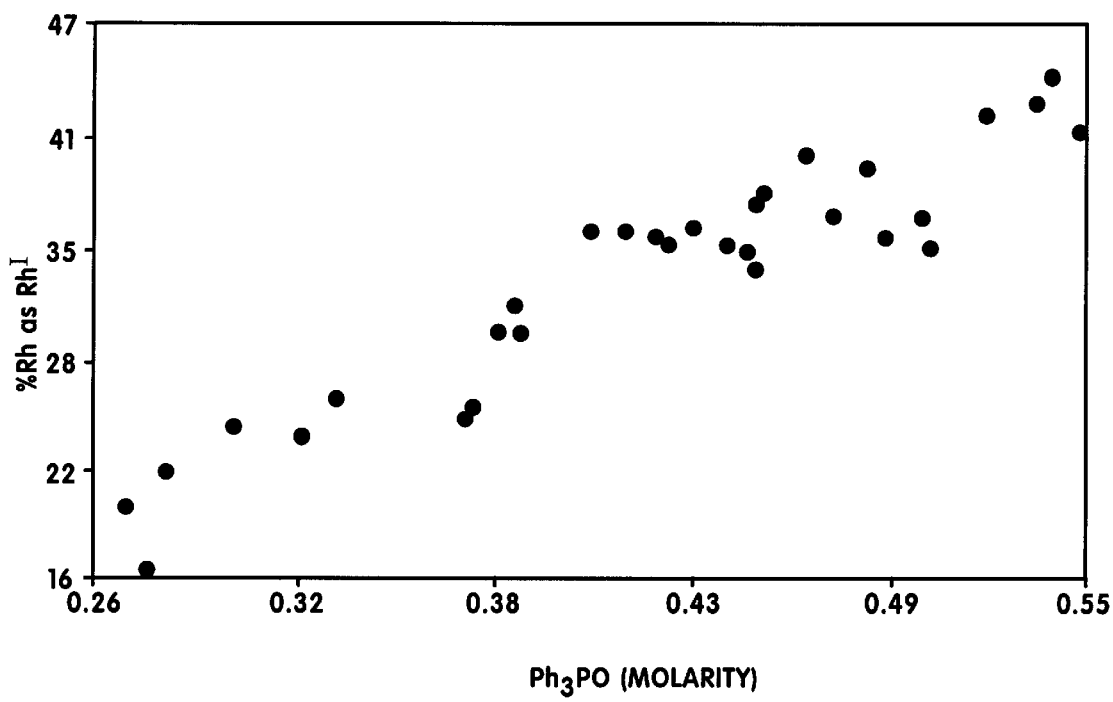
FIG. 25 is a correlation plot of continuous bench scale reactor on-line infrared data for active rhodium species (Rh$^f$) concentration as a function of triphenyl phosphine oxide (Ph$_3$PO) concentration.
Figure 26:
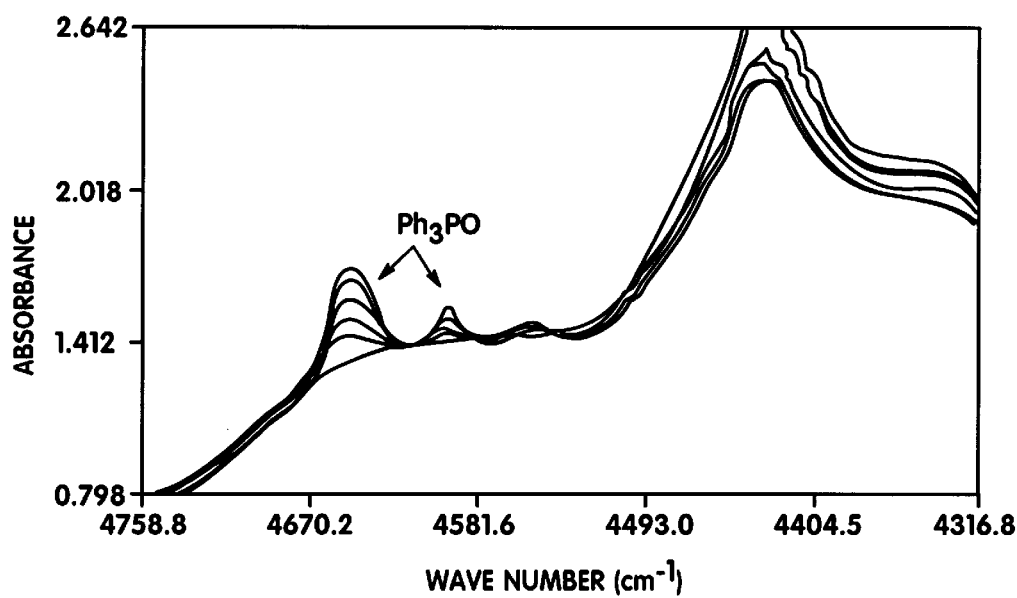
FIG. 26 is an overlay of on-line extended mid-infrared spectra for triphenyl phosphine oxide (Ph$_3$PO)

An illustration of the effect of triphenyl phosphine oxide concentration on $Rh^I$ concentration as determined by on-line infrared analysis is shown in FIG. 25. Over an eight-hour period in the continuous bench scale reactor, triphenyl phosphine oxide concentration was increased from 0.25 molar to 0.55 molar under reactor conditions as outlined below:

Temperature=185° C.
Pressure=400 psig
Water 2.8 molar
Total rhodium=3.5 millimolar
No Methanol feed FIG. 25 contains about 35 data points removed from the trend file for clarity. As in the case of water in Example 3, a direct dependence of Rh as $Rh^I$ on triphenyl phosphine oxide concentration is observed. FIG. 26 contains several overlaid spectra from the extended mid-infrared region showing the increase in triphenyl phosphine oxide concentration. As in the previous example, this example serves to show the intimate correlations between reactor solution components that can be deduced from on-line infrared analysis. This example shows that the triphenyl phosphine oxide concentration can be tuned to achieve a desired $Rh^I$ concentration. As in the previous example, the ability to determine the absolute value of %Rh as $Rh^I$ as shown in FIG. 25 demonstrates an advantage of the invention and is only a function of the specific reactor conditions used in this example.

Example 9

The water gas shift reaction involving the rhodium catalyzed formation of carbon dioxide and hydrogen gas from carbon monoxide and water is an undesirable side reaction in acetic acid processing via methanol carbonylation. It increases carbon monoxide usage rates and decreases catalyst stability. The ability to precisely and accurately monitor on a frequent basis the components that influence the WGS rate can lead to appropriate algorithms to be built into process control to allow optimal run conditions to be achieved and maintained. Maintenance of such conditions can lead to higher production rates, lower raw material usage rates and lower catalyst usage rates. The effect of several reactor solution components on WGS rate are shown in the experiments below.

(a) In a continuous bench scale reactor experiment under reactor conditions given below, water concentration was allowed to decrease from 7 molar to 5 molar over a three-hour period and the effect on the WGS reaction (as a function of solution $CO_2$) was tracked by on-line infrared analysis. Sampling and analysis frequency was approximately 30 times per hour.

Figure 27:
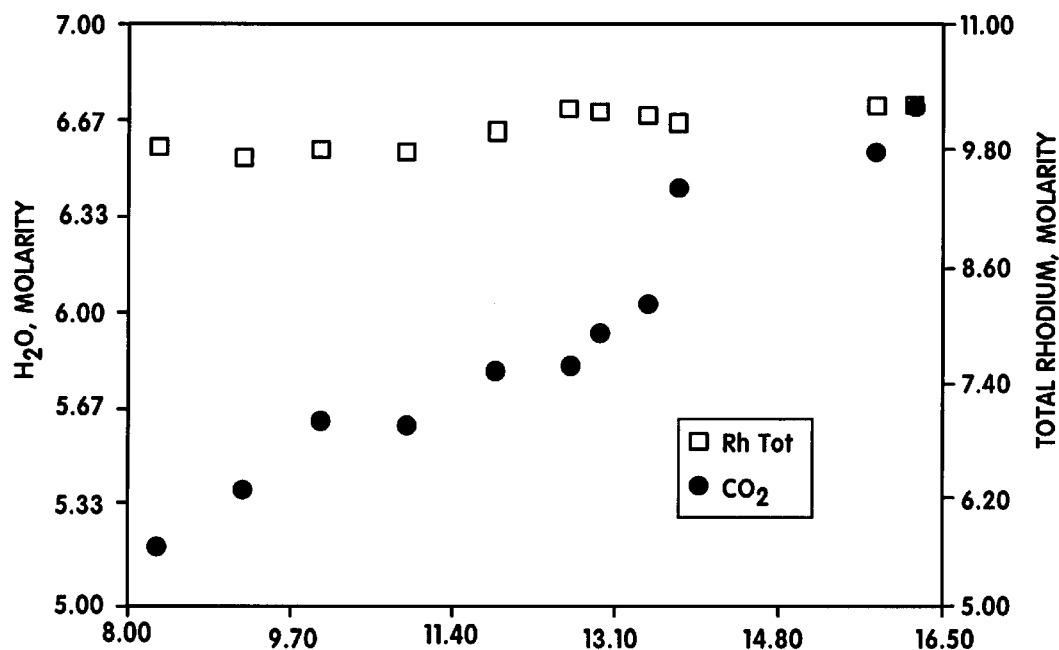
FIG. 27 is a correlation plot of continuous bench scale reactor on-line infrared data for the water gas shift reaction represented by change in CO$_2$ content at constant rhodium concentration, as a function of water concentration.

Temperature=185° C.
Pressure=400 psig
Triphenyl phosphine oxide=0.30 molar
Rhodium=10.5 molar
Methyl iodide=0.85 molar
Methanol feed rate=320 g/hr The data are presented in graphical format in FIG. 27 and show that at constant rhodium concentration, the WGS rate increases linearly with water concentration.

Figure 28:
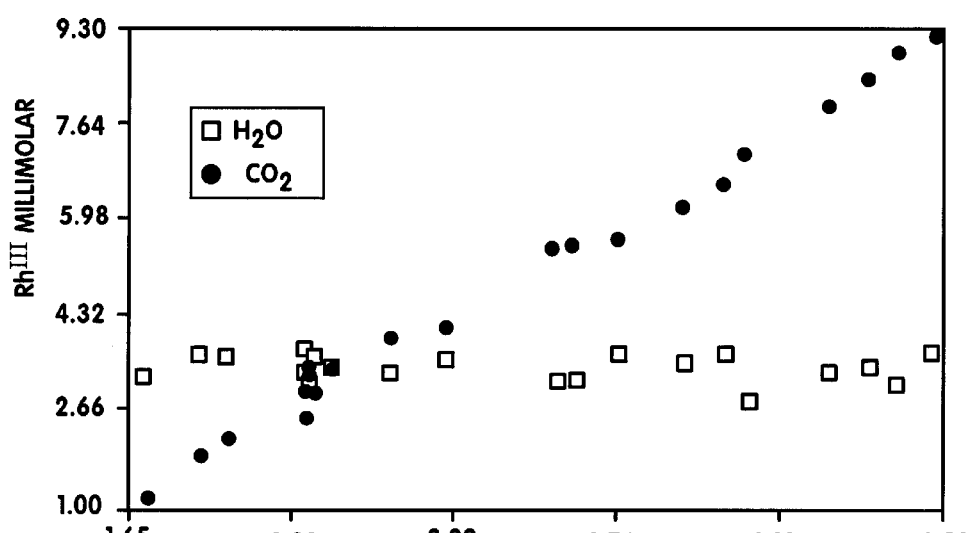
FIG. 28 is a correlation plot of continuous bench scale reactor on-line infrared data for the water gas shift reaction represented by change in CO$_2$ content as a function of rhodium concentration.
Figure 29:
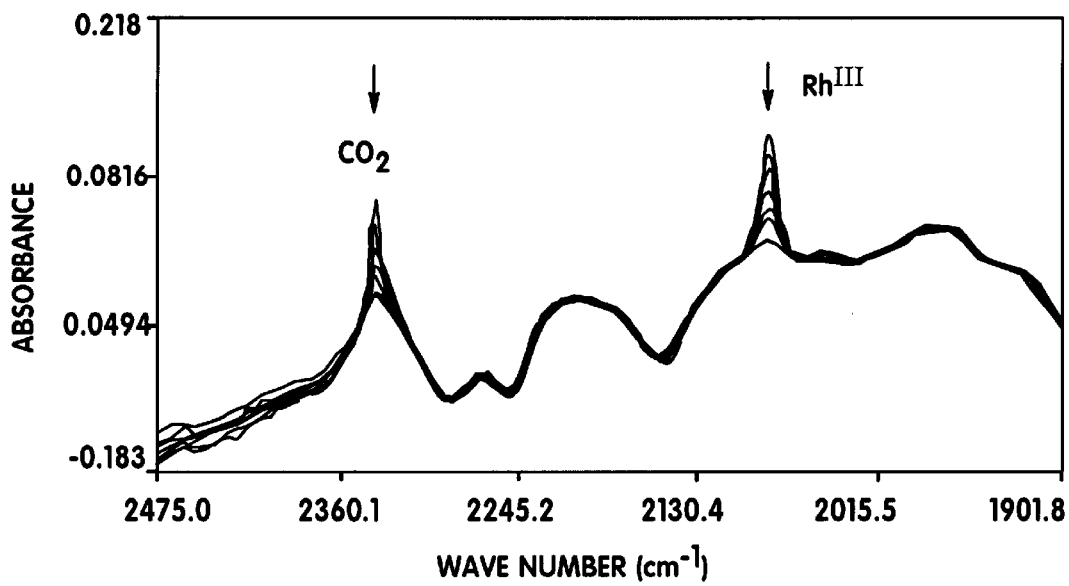
FIG. 29 is an overlay of on-line infrared spectra for water gas shift reaction represented by change in CO$_2$ content as a function of rhodium concentration.

(b) In this experiment reactor conditions were as follows:
Temperature=185° C.
Pressure=400 psig
Triphenyl phosphine oxide=0.0 molar
Methyl iodide=0.0–0.2 molar
$I^-$=0.4–0.6 molar $H_2O$=3.5 molar No Methanol feed In this experiment, rhodium was allowed to decay under conditions which are highly undesirable for catalyst stability. This decay was allowed to occur at a constant water concentration to examine the effect of rhodium concentration on WGS rate. The data are presented in graphical format in FIG. 28 and in overlaid spectral format in FIG. 29. Both Figures show the linear decrease in solution carbon dioxide with decreasing rhodium concentration.

Figure 30:
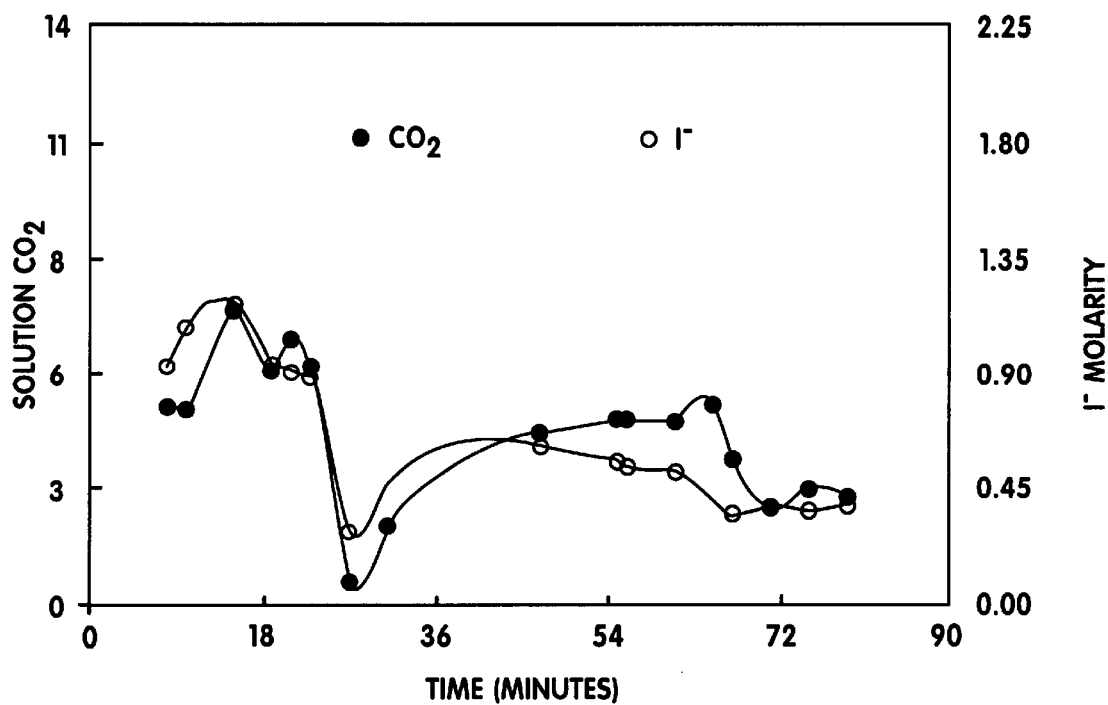
FIG. 30 is a correlation plot of continuous bench scale reactor on-line infrared data for the water gas shift reaction represented by change in CO$_2$ content as a function of ionizable iodide (I$^-$) concentration.

(c) This experiment involves reactor startup, i.e., from ambient conditions and no raw material feeds to process conditions with established feeds. Reactor solution component concentrations can vary considerably during startup due to shifts in various dependent equilibria until stable operating conditions are established. Data was chosen from a single representative ninety-minute period when water and rhodium concentration remained relatively constant but the methyl iodide/ionizable iodide ($I^-$) ratio varied considerably. This allowed the effect of $I^-$ on WGS rate to be determined. The plot shown in FIG. 30 indicates that solution carbon dioxide closely tracks $I^-$ concentration. This is consistent with the mechanism of the WGS reaction and again shows the advantage of employing on-line infrared data in tracking and potentially controlling an acetic process.

Example 10

A continuous bench scale reactor was run for two weeks under the conditions set out below:

Reactor temperature=187° C.–189° C.

Reactor pressure=400 psig (130 psig CO)

Triphenyl phosphine oxide=0.5 molar

Water concentration=3.5–4.5 molar

Methyl iodide concentration=0.9–1.2 molar

Rhodium concentration=4.0–6.5 millimolar

Methanol feed rate=220–380 g/hr

Methyl acetate=0.1–0.6 molar

The process was automatically controlled from data generated by an on-line infrared analyzer as described previously. A 0.5 mm pathlength transmission cell with sapphire windows was used to carry out the analysis of triphenyl phosphine oxide, water, methyl iodide and methyl acetate in the extended mid-infrared region. A 0.075 mm pathlength transmission cell with sapphire windows was used to analyze both rhodium and solution carbon dioxide in the mid-infrared region.

As those skilled in the art of acetic acid manufacturing are aware and as described previously, the water gas shift (WGS) reaction is an undesired side reaction producing hydrogen and carbon dioxide. The rate of the WGS reaction is related to the concentrations of rhodium, water, methyl iodide and methyl acetate by virtue of the fact that there are multiple complex dependencies among these variables. Thus, the more of these variables that can be monitored simultaneously in real time, the better the control of the process would be anticipated. Rhodium, water and methyl iodide are typically added to the process to maintain their desired concentrations, whereas methyl acetate may be added or generated in situ. The benefits of real time analysis of rhodium, water and methyl iodide have already been described. The methyl acetate concentration is a function of the concentrations of the other three added components and also of reactor temperature and of feed rate. The number of dependent variables renders more complex the process of inferring, estimating or deriving an instantaneous methyl acetate concentration from the measured concentrations of other components. Typically, higher methyl acetate concentrations are associated with lower WGS rates and thus, availability of real time reactor methyl acetate concentrations would aid in control of this side reaction.

Figure 31:
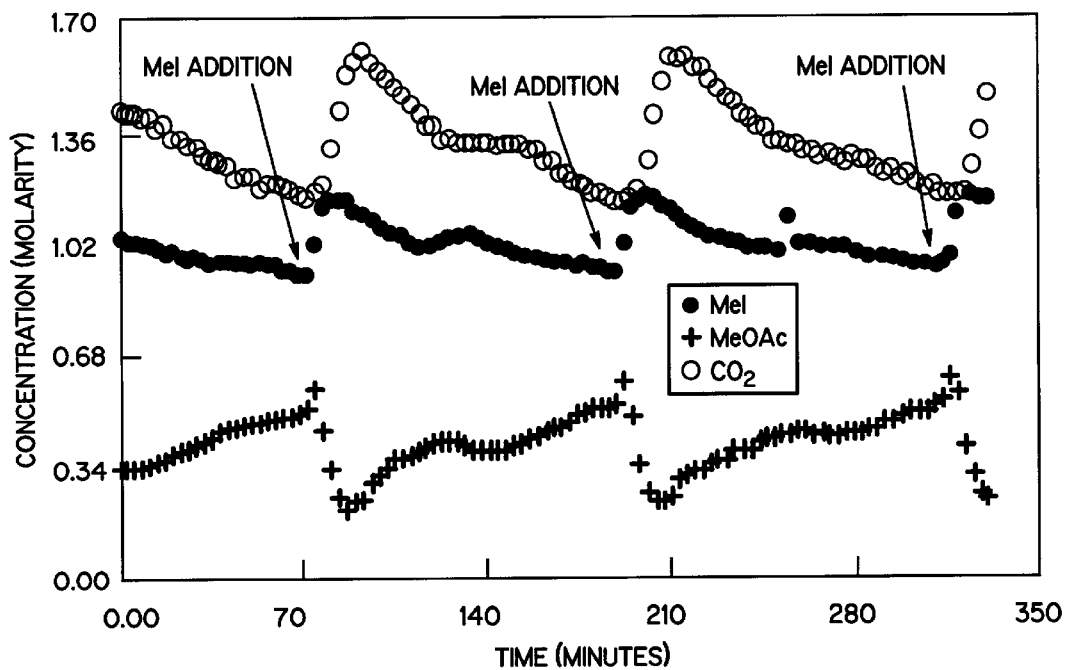
FIG. 31 is a multi-component trend file containing 6 hours of run time data for three reactor solution components.

FIG. 31 represents about 120 data points from a six hour period of on-line analyzer run time data. In this period rhodium and water were controlled at 4 millimolar and 4 molar respectively. To illustrate the spirit of the invention, methyl iodide was given generous control limits of 0.90–1.20 molar. With rhodium and water at constant concentration and at constant methanol feed rate and reactor temperature, those skilled in the art of acetic acid manufacture would expect methyl acetate concentration to increase with decreasing methyl iodide concentration. This is evidenced in the Figure as methyl iodide decay leads to an increase in methyl acetate with subsequent additions of methyl iodide leading to a decrease of methyl acetate. Solution carbon dioxide (indicative of WGS) measured simultaneously in the 0.075 mm cell in the mid-infrared and included in FIG. 31 shows the expected inverse dependence on methyl acetate concentration. By corollary, control limits could have been set for methyl acetate rather than methyl iodide in the above example and automated additions of methyl iodide would have been made in response to these control limits.

A further use of on-line methyl acetate analysis can be inferred from the above data. Two different cells gave information relating to the WGS reaction or to the selectivity. The mid-infrared cell gave direct information from the solution carbon dioxide trend data, while the extended mid-infrared cell gave indirect information from the methyl acetate trend data. This is a good example of how a built in redundancy can be used as a cross-check or diagnostic method to ensure that both cells are providing valid data. Any large deviation from an inverse relationship between solution carbon dioxide and methyl acetate concentrations could indicate an electronic, cell or interferant problem.

Propionic acid, an impurity in acetic acid, is formed in the reactor. As end users of acetic acid have certain specifications on allowable propionic acid and as the selling price may be dependent on product purity, it is important to control the rate of formation of this byproduct in the reactor. Those skilled in the art of acetic acid manufacture are aware that propionic acid formation is a function of hydrogen formation in the previously described competing water gas shift (WGS) reaction.

Figure 32:
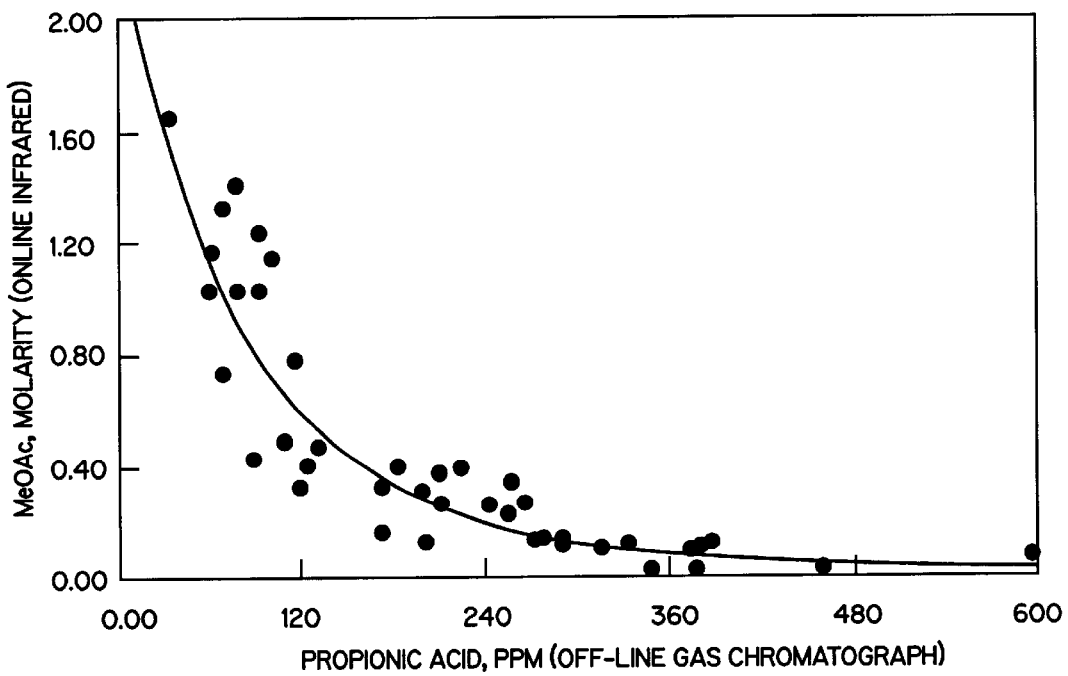
FIG. 32 is a correlation plot showing the effect of methyl acetate as measured by on-line infrared on propionic acid as measured by off-line gas chromatography.

The plot in FIG. 32 shows the correlation between on-line methyl acetate measurements and propionic acid concentration in manual reactor samples taken over a several week period as determined by gas chromatography and illustrates that control of propionic acid concentration can be achieved by controlling methyl acetate concentration.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, a single cell or two cell infrared system may be successfully utilized in the present invention. Moreover, an iridium-catalyzed carbonylation system may be used in accordance with the principles of the present invention rather that a rhodium-catalyzed carbonylation system. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A method of effecting process control in a reaction for the production of acetic acid, comprising:
   collecting a sample of an acetic acid reaction mixture containing at least methyl iodide, water, methyl acetate and an active catalyst species of a catalyst selected from the group consisting of rhodium and iridium;
   measuring the concentration of methyl iodide, water, methyl acetate and the active catalyst species in an infrared analyzer; and
   adjusting the concentration of at least methyl iodide, water and the active catalyst species in the acetic acid reaction mixture in response to the measured concentrations of methyl iodide, water, methyl acetate and active catalyst species.

2. The method of claim 1 wherein the infrared analyzer is a Fourier Transform infrared spectrometer.

3. The method of claim 1 further comprising measuring the concentration of methyl iodide in an infrared cell operating in a range selected from the group consisting of a mid-infrared region, an extended mid-infrared region, and combinations thereof.

4. The method of claim 1 further comprising measuring the concentration of water in an infrared cell operating in a range selected from the group consisting of a mid-infrared region, an extended mid-infrared region, and combinations thereof.

5. The method of claim 1 further comprising measuring the concentration of methyl acetate in an infrared cell operating in a range selected from the group consisting of a mid-infrared region, an extended mid-infrared region, and combinations thereof.

6. The method of claim 1 further comprising measuring the concentration of active catalyst species in an infrared cell operating in a mid-infrared region.

7. The method of claim 6 wherein the active catalyst species is of a rhodium catalyst.

8. The method of claim 1 wherein adjusting the concentration of at least methyl iodide, water and the active catalyst species in the acetic acid reaction mixture produces a substantially constant concentration for each of methyl iodide, water, methyl acetate and active catalyst species during the manufacture of acetic acid.

9. The method of claim 8 wherein the active catalyst species is of a rhodium catalyst.

10. The method of claim 1 wherein the frequency of measuring the concentration of methyl iodide, water, methyl acetate and the active catalyst species is at least about 30 times per hour.

11. The method of claim 1 further comprising controlling the sample temperature in a range between about 20° C. and about 130° C.

12. The method of claim 1 wherein the infrared analyzer contains a first cell operating in a mid-infrared region and a second cell operating in an extended mid-infrared region.

13. The method of claim 12 wherein the infrared analyzer utilizes a single polychromatic light source.

14. The method of claim 1 further comprising transmitting the measured concentrations to a control unit.

15. The method of claim 1 wherein the acetic acid reaction mixture contains a Group 15 oxide of the formula $R_3M=O$, wherein M is an element from Group 15 of Periodic Table and each R is independently a substituted or unsubstituted alkyl, aryl, aralkyl or alkaryl group.

16. The method of claim 15 further comprising measuring the concentration of the Group 15 oxide in the infrared analyzer.

17. The method of claim 16 further comprising measuring the concentration of Group 15 oxide in an infrared cell operating in a range selected from the group consisting of a mid-infrared region, an extended mid-infrared region, and combinations thereof.

18. The method of claim 16 farther comprising adjusting the concentration of the Group 15 oxide.

19. The method of claim 15 wherein M is phosphorus.

20. The method of claim 19 wherein $R_3M=O$ is triphenyl phosphine oxide.

21. The method of claim 1 wherein the infrared analyzer is on-line with a reactor containing the acetic acid reaction mixture.

22. The method of claim 1 wherein the infrared analyzer is offline from a reactor containing the acetic acid reaction mixture.

23. A method of manufacturing acetic acid with improved process control, comprising:
   collecting a sample of an acetic acid reaction mixture containing at least methyl iodide, water, methyl acetate and an active catalyst species of a catalyst selected from the group consisting of rhodium and iridium;
   measuring the concentration of methyl iodide, water, methyl acetate and the active catalyst species in an infrared analyzer;
   adjusting the concentration of at least methyl iodide, water and the active catalyst species in the acetic acid reaction mixture in response to the measured concentrations of methyl iodide, water, methyl acetate and active catalyst species; and
   manufacturing acetic acid thereby.

24. The method of claim 23 wherein the infrared analyzer is a Fourier Transform infrared spectrometer.

25. The method of claim 23 further comprising measuring the concentration of methyl iodide in an infrared cell operating in a range selected from the group consisting of a mid-infrared region, an extended mid-infrared region, and combinations thereof.

26. The method of claim 23 further comprising measuring the concentration of water in an infrared cell operating in a range selected from the group consisting of a mid-infrared region, an extended mid-infrared region, and combinations thereof.

27. The method of claim 23 further comprising measuring the concentration of methyl acetate in an infrared cell operating in a range selected from the group consisting of a mid-infrared region, an extended mid-infrared region, and combinations thereof.

28. The method of claim 23 further comprising measuring the concentration of active catalyst species in an infrared cell operating in a mid-infrared region.

29. The method of claim 28 wherein the active catalyst species is of a rhodium catalyst.

30. The method of claim 23 wherein adjusting the concentration of at least methyl iodide, water and the active catalyst species in the acetic acid reaction mixture produces a substantially constant concentration for each of methyl iodide, water, methyl acetate and active catalyst species during the manufacture of acetic acid.

31. The method of claim 30 wherein the active catalyst species is of a rhodium catalyst.

32. The method of claim 23 wherein the frequency of measuring the concentration of methyl iodide, water, methyl acetate and the active catalyst species is at least about 30 times per hour.

33. The method of claim 23 further comprising controlling the sample temperature in a range between about 20° C. and about 130° C.

34. The method of claim 23 wherein the infrared analyzer contains a first cell operating in a mid-infrared region and a second cell operating in an extended mid-infrared region.

35. The method of claim 34 wherein the infrared analyzer utilizes a single polychromatic light source.

36. The method of claim 23 further comprising transmitting the measured concentrations to a control unit.

37. The method of claim 23 wherein the acetic acid reaction mixture contains a Group 15 oxide of the formula $R_3M=O$, wherein M is an element from Group 15 of Periodic Table and each R is independently a substituted or unsubstituted alkyl, aryl, aralkyl or alkaryl group.

38. The method of claim 37 further comprising measuring the concentration of the Group 15 oxide in the infrared analyzer.

39. The method of claim 38 further comprising measuring the concentration of Group 15 oxide in an infrared cell operating in a range selected from the group consisting of a mid-infrared region, an extended mid-infrared region, and combinations thereof.

40. The method of claim 38 further comprising adjusting the concentration of the Group 15 oxide.

41. The method of claim 37 wherein M is phosphorus.

42. The method of claim 41 wherein $R_3M=O$ is triphenyl phosphine oxide.

43. The method of claim 23 wherein the infrared analyzer is on-line with a reactor containing the acetic acid reaction mixture.

44. The method of claim 23 wherein the infrared analyzer is offline from a reactor containing the acetic acid reaction mixture.

45. A method of effecting process control in a reaction for the production of acetic acid, comprising:

collecting a sample of acetic acid reaction mixture containing at least methyl iodide, water, methyl acetate and an active rhodium species;

measuring the concentration of methyl iodide in an infrared cell operating in a range selected from the group consisting of the mid-infrared region, the extended mid-infrared region, and combinations thereof;

measuring the concentration of water in an infrared cell operating in a range selected from the group consisting of the mid-infrared region, the extended mid-infrared region, and combinations thereof;

measuring the concentration of methyl acetate in an infrared cell operating in a range selected from the group consisting of the mid-infrared region, the extended mid-infrared region, and combinations thereof;

measuring the concentration of active rhodium species in an infrared cell operating in a mid-infrared region; and adjusting the concentration of at least methyl iodide, water and the active catalyst species in the acetic acid reaction mixture in response to the measured concentrations of methyl iodide, water, methyl acetate and active rhodium species to produce a substantially constant concentration for each of methyl iodide, water, methyl acetate and active rhodium species during the manufacture of acetic acid.

* * * * *

UNITED STATES PATENT AND TRADEMARK OFFICE
CERTIFICATE OF CORRECTION

PATENT NO.    : 6,362,366 B1
DATED         : March 26, 2002
INVENTOR(S)   : Hallinan et al.

It is certified that error appears in the above-identified patent and that said Letters Patent is hereby corrected as shown below:

Column 4,
Line 63, "$Rh(CO)I_{4-}$," should be -- $Rh(CO)I_4^-$, --.

Column 6,
Line 65, "$RhCl_3 . 3H_2O$; $RhBr_3 . 3H_2O$; $RhI_3 . 3H_2O$" should be -- $RhCl_3 \bullet 3H_2O$; $RhBr_3 \bullet 3H_2O$; $RhI_3 \bullet 3H_2O$ --.

Column 7,
Line 1, "$Rh[ (C_6H_5)P)]_2(CO)Cl$;" should be -- $Rh[(C_6H_5)P]_2(CO)Cl$; --

Column 8,
Line 59, "are" should be -- is --.
Line 60, "are" should be -- is --.

Column 9,
Line 52, "encompasses portion" should be -- encompasses a portion --.

Column 12,
Line 3, "water an methyl acetate" should be -- water and methyl acetate --.

Column 18,
Line 62, "multi component" should be -- multi-component --.

Column 26,
Line 9, "farther" should be -- further --.

Signed and Sealed this

Twentieth Day of August, 2002

Attest:

JAMES E. ROGAN
Attesting Officer      Director of the United States Patent and Trademark Office